US008481471B2

(12) United States Patent
Smith et al.

(10) Patent No.: US 8,481,471 B2
(45) Date of Patent: *Jul. 9, 2013

(54) METHOD OF USING SOLID-LAYERED BLEACH COMPOSITIONS

(71) Applicant: The Clorox Company, Oakland, CA (US)

(72) Inventors: William L. Smith, Pleasanton, CA (US); Evan M. Rumberger, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/720,753

(22) Filed: Dec. 19, 2012

(65) Prior Publication Data

US 2013/0109609 A1 May 2, 2013

Related U.S. Application Data

(63) Continuation of application No. 12/943,117, filed on Nov. 10, 2010, now Pat. No. 8,361,944, which is a continuation-in-part of application No. 12/620,932, filed on Nov. 18, 2009, now Pat. No. 8,287,755.

(60) Provisional application No. 61/121,029, filed on Dec. 9, 2008.

(51) Int. Cl.
*A61Q 11/02* (2006.01)
*A61Q 11/00* (2006.01)
*A61K 8/20* (2006.01)
*C01B 11/06* (2006.01)

(52) U.S. Cl.
USPC ........... 510/116; 510/117; 510/298; 510/302; 510/349; 510/380; 510/446; 252/187.27; 252/187.28; 252/187.3; 252/186.37; 422/28; 422/29

(58) Field of Classification Search
USPC ............... 252/187.27, 187.28, 187.29, 187.3, 252/186.37; 510/116, 117, 298, 302, 349, 510/380, 446; 422/28, 29
See application file for complete search history.

(56) References Cited

U.S. PATENT DOCUMENTS

| 1,471,987 | A |   | 10/1923 | Vogt |   |
|---|---|---|---|---|---|
| 1,481,003 | A | * | 1/1924 | Gegenheimer | 252/186.37 |
| 1,961,576 | A | * | 6/1934 | Taylor | 252/186.37 |
| 2,409,718 | A |   | 11/1941 | Snell et al. |   |
| 2,320,279 | A |   | 5/1943 | Kalusdian |   |
| 2,498,344 | A |   | 2/1950 | Rider et al. |   |
| 2,921,911 | A |   | 1/1960 | Staubly et al. |   |
| 3,113,111 | A |   | 12/1963 | Myerson |   |
| 3,257,450 | A |   | 6/1966 | Globus |   |
| 3,337,466 | A |   | 8/1967 | Puetzer et al. |   |
| 3,342,674 | A | * | 9/1967 | Kowalski | 424/661 |
| 3,446,893 | A | * | 5/1969 | Hanford et al. | 424/76.3 |
| 3,640,879 | A |   | 2/1972 | Fitzgerald, Jr. |   |
| 3,755,179 | A |   | 8/1973 | Fitzgerald, Jr. |   |
| 3,769,224 | A | * | 10/1973 | Inamorato | 510/302 |
| 3,793,211 | A |   | 2/1974 | Kohlhepp et al. |   |
| 3,821,117 | A |   | 6/1974 | Breece et al. |   |
| 3,936,385 | A |   | 2/1976 | Cheng |   |
| 4,035,484 | A | * | 7/1977 | Faust et al. | 424/665 |
| RE29,473 | E |   | 11/1977 | Fitzgerald, Jr. |   |
| 4,082,841 | A |   | 4/1978 | Pader |   |
| 4,087,360 | A | * | 5/1978 | Faust et al. | 210/701 |
| 4,146,676 | A |   | 3/1979 | Saeman et al. |   |
| 4,256,599 | A | * | 3/1981 | Krisp et al. | 510/117 |
| 4,276,349 | A |   | 6/1981 | Saeman |   |
| 4,362,639 | A |   | 12/1982 | Eoga |   |
| 4,421,664 | A |   | 12/1983 | Anderson et al. |   |
| 4,552,679 | A |   | 11/1985 | Schobel et al. |   |
| 4,657,784 | A |   | 4/1987 | Olson |   |
| 4,671,972 | A | * | 6/1987 | Schobel et al. | 427/213 |
| 4,692,335 | A |   | 9/1987 | Iwanski |   |
| 4,707,160 | A |   | 11/1987 | Chun et al. |   |
| 4,731,195 | A |   | 3/1988 | Olson |   |
| 4,933,102 | A |   | 6/1990 | Olson |   |
| 4,961,872 | A |   | 10/1990 | Sinclair |   |
| 5,114,647 | A |   | 5/1992 | Levesque et al. |   |
| 5,133,892 | A |   | 7/1992 | Chun et al. |   |
| 5,407,598 | A | * | 4/1995 | Olson et al. | 252/186.35 |

(Continued)

FOREIGN PATENT DOCUMENTS

| GB | 490384 | 8/1938 |
| GB | 550020 | 12/1942 |
| GB | 552803 | 4/1943 |
| GB | 606431 | 8/1948 |
| GB | 739046 | 10/1955 |
| WO | WO 01/36115 | 5/2001 |
| WO | WO 2010/077468 | 7/2010 |

OTHER PUBLICATIONS

International Search Report of PCT Application No. PCT/US2009/065090, Jan. 21, 2010, 3 pgs.
International Search Report of PCT Application No. PCT/US2010/052602, Dec. 9, 2010, 3 pgs.
International Search Report of PCT Application No. PCT/US2010/52487, Jan. 4, 2011, 3 pgs.
International Search Report of PCT Application No. PCT/US2010/56117, Jan. 14, 2011, 3 pgs.
International Search Report of PCT Application No. PCT/US2010/56139, Jan. 18, 2011, 3 pgs.

*Primary Examiner* — Joseph D Anthony
(74) *Attorney, Agent, or Firm* — Alok Goel; Stacy Hegle Combs

(57) ABSTRACT

The present invention provides a solid-layered composition having at least two parts. The first part comprises a) calcium hypochlorite, magnesium hypochlorite and mixtures thereof, b) a builder, c) a water-soluble polymer, d) an acid, and e) wherein the first part does not contain sodium hypochlorite, lithium hypochlorite, potassium hypochlorite and mixtures thereof. The second part comprises a) a functional ingredient, b) a builder or filler, and c) wherein the second part does not contain any oxidant.

20 Claims, No Drawings

U.S. PATENT DOCUMENTS

| | | | |
|---|---|---|---|
| 5,534,178 A | 7/1996 | Bailly et al. | |
| 5,599,781 A | 2/1997 | Haeggberg et al. | |
| 5,753,602 A | 5/1998 | Hung et al. | |
| 5,869,438 A | 2/1999 | Svendsen et al. | |
| 5,981,457 A | 11/1999 | Ahmed | |
| 6,071,539 A * | 6/2000 | Robinson et al. | 424/466 |
| 6,146,538 A * | 11/2000 | Martin | 210/698 |
| 6,211,129 B1 | 4/2001 | Gladfelter et al. | |
| 6,298,871 B1 * | 10/2001 | Pickens et al. | 137/268 |
| 6,358,909 B1 | 3/2002 | Ochomogo | |
| 6,426,111 B1 * | 7/2002 | Hirsch | 426/590 |
| 6,468,950 B1 | 10/2002 | Kawasaki et al. | |
| 6,589,443 B1 * | 7/2003 | Olson et al. | 252/186.2 |
| 6,852,238 B2 | 2/2005 | Connelly, Jr. | |
| 6,863,830 B1 | 3/2005 | Purdy et al. | |
| 6,969,527 B2 | 11/2005 | Brennan et al. | |
| 6,995,129 B2 | 2/2006 | Olson et al. | |
| 7,309,444 B2 * | 12/2007 | Connelly, Jr. | 210/753 |
| 7,410,938 B2 | 8/2008 | Brennan | |
| 7,517,413 B2 | 4/2009 | van Buskirk et al. | |
| 8,361,942 B2 * | 1/2013 | Smith et al. | 252/187.27 |
| 8,361,943 B2 * | 1/2013 | Smith et al. | 252/187.27 |
| 8,361,944 B2 * | 1/2013 | Smith et al. | 252/187.27 |
| 8,361,945 B2 * | 1/2013 | Smith et al. | 252/187.27 |
| 2002/0189634 A1 | 12/2002 | Vanhauwermeiren et al. | |
| 2002/0198128 A1 | 12/2002 | Perkins et al. | |
| 2003/0086878 A1 * | 5/2003 | Rajaiah et al. | 424/49 |
| 2004/0081690 A1 * | 4/2004 | Gauthier et al. | 424/465 |
| 2004/0082491 A1 * | 4/2004 | Olson et al. | 510/375 |
| 2004/0266650 A1 | 12/2004 | Lambotte et al. | |
| 2005/0143274 A1 | 6/2005 | Ghosh et al. | |
| 2005/0233900 A1 | 10/2005 | Smith et al. | |
| 2005/0288209 A1 | 12/2005 | Fletcher | |
| 2006/0258553 A1 | 11/2006 | Catalfamo et al. | |
| 2008/0083071 A1 * | 4/2008 | Tremblay et al. | 8/109 |
| 2008/0166176 A1 | 7/2008 | Rees et al. | |
| 2009/0042756 A1 | 2/2009 | Muzik et al. | |
| 2009/0148342 A1 | 6/2009 | Bromberg et al. | |
| 2009/0165818 A1 | 7/2009 | Smith et al. | |
| 2010/0140544 A1 | 6/2010 | Smith et al. | |

\* cited by examiner

METHOD OF USING SOLID-LAYERED BLEACH COMPOSITIONS

CROSS-REFERENCES TO RELATED APPLICATIONS

This application is a continuation of U.S. Ser. No. 12/943,117, filed on Nov. 10, 2010, now U.S. Pat. No. 8,361,944, which is a continuation-in-part of U.S. Ser. No. 12/620,932, filed on Nov. 18, 2009, now U.S. Pat. No. 8,287,755, which claims the benefit of provisional U.S. Application No. 61/121,029, filed on Dec. 9, 2008. Each of the above patent matters are hereby incorporated by reference in their entirety.

BACKGROUND OF THE INVENTION

1. Field of the Invention

The present invention relates generally to solid-layered bleach compositions and methods of use. These bleach compositions are used to clean and disinfect a variety of substances. These surfaces include, but are not limited to, water, wastes, wastewater, produce, poultry, meat, soil, plants, hard surfaces, soft surfaces, textiles, medical devices and appliances. They can be also used for therapeutic treatment of human and animal skin, nails, teeth, gums, burns, wounds, ears, nasal or oral cavities. They may also be used to inhibit the growth of mold and to remove odors.

2. Description of the Related Art

Solid bleach compositions have progressed for decades and created a large chemical industry devoted to cleaning and disinfecting. N-Chloro hydantoins, N-chloro isocyanurates, sodium hypochlorite, and calcium hypochlorite are used quite frequently in bleach compositions for many companies because they are cheap to produce and they are highly effective. However, these bleach compositions have several disadvantages that limit their usefulness. Sodium hypochlorite is only available as a liquid at room temperature. Calcium hypochlorite leaves residue. Chlorinated hydantoins and isocyanurates lack long term solution stability and generate malodor. All these disadvantages present compositions which consumers may not prefer.

It is also quite desirable to include functional ingredients in the solid bleach compositions that may react with or have poor compatibility with the bleach. Such functional ingredients may provide a pleasant fragrance, improve soil removal increase wetting, inhibit corrosion, or provide other desirable benefits. Either the bleach or the functions ingredient may typically be coated, encapsulated or embedded in a polymer, resin, or a wax to improve the stability and shelf-life of the composition. However this approach also increases cost, complexity, and the time required for the composition to dissolve in water and produced the desired function.

The presently claimed invention solves some of these problems. Use of calcium hypochlorite in at least a two-part system does not leave residues that are associated with other calcium hypochlorite compositions, nor do they generate malodors typically associated with the use of chlorinated isocyanurates. The present invention also releases bleach faster than the typical use of halogenated hydantoins. The present invention also dissolves faster than typical commercial products based on calcium hypochlorite or halogenated hydantoins. The current invention has none of its ingredients coated, encapsulated, or embedded in a polymer, resin, or a wax. It is therefore an object of the present invention to provide a solid-layered bleach composition and methods of use that overcomes the disadvantages and shortcomings associated with prior art solid bleach compositions.

SUMMARY OF THE INVENTION

In accordance with the above objects and those that will be mentioned and will become apparent below, one aspect of the present invention comprises a solid-layered bleach composition having at least two parts comprising a first part and a second part: wherein said first part comprising, a) 0.001%-50% of a hypochlorite selected from the group consisting of calcium hypochlorite, magnesium hypochlorite and mixtures thereof; b) a builder selected from the group consisting of carbonate, bicarbonate, sesquicarbonate and mixtures thereof; c) a water-soluble polymer selected from the group consisting of a polycarboxylate, sulfonated carboxylate, polysulfonate, polyvinylpyrrolidone, polyquaternary ammonium salts, copolymers and mixtures thereof; d) an acid selected from the group consisting of sulfonic acid, polysulfonic acid, carboxylic acid, dicarboxylic acid, polycarboxylic acid, acid sulfate, acid phosphate, phosphonic acid, and mixtures thereof; e) optionally a filler selected from the group consisting of chloride, sulfate, phosphate, silicate, borate, nitrate, chlorate, aluminate, silica-aluminate, hydroxide, and oxide compounds of alkali, metals, alkaline earths, aluminum, zinc and tin including hydrates, mono, di and tribasic compounds, mixed salts, borates, clays, zeolites and mixtures thereof; f) optionally, a water-swellable polymer selected from the group consisting of cross-linked polycarboxylate, cross-linked polysulfonate, cross-linked carboxymethyl cellulose, cellulose, sodium carboxymethylcellulose, and mixtures thereof; g) optionally, desiccants, solid processing aids, colorants, agglomeration aids, binders, glidants, corrosion inhibitors, and mixtures thereof; and h) wherein the first part does not contain sodium hypochlorite, lithium hypochlorite, potassium hypochlorite, sodium chlorite, chlorine dioxide, N-halogenated compounds, hydantoins, isocyanurates, carboxylic acids that also have hydroxyl, amino, amido, imino, or imido groups, enzymes, and mixtures thereof; and wherein the second part comprising, a) a functional ingredient selected from the group consisting of a surfactant, a hydrotrope, a wetting agent, a dispersant, a penetrant, a chelating agent, an odor absorbent, a fragrance, a flavoring agent, a sweetener, a colorant, a corrosion inhibitor, a viscosity modifier, a foam booster, a defoamer, a stain and soil repellant, a fluorescent whitening agent, an enzyme, a cloud point modifier, an anti-microbial agent, a sporulation agent, a catalyst or an activating agent, a therapeutic agent, and mixtures thereof; b) a builder or filler selected from the group consisting of a carbonate, a bicarbonate, a sesquicarbonate, a chloride, a sulfate, a phosphate, a silicate, borate, a nitrate, an aluminate, a silica-aluminate, a hydroxide, or an oxide compound of alkali metals, alkaline earths, aluminum, zinc and tin including hydrates, mono, di and tribasic compounds, mixed salts, a borate, a clay, a zeolite, and mixtures thereof; c) optionally acids, water soluble polymers, disintegrants, desiccants, solid processing aids, agglomeration aids, binders, glidants, preservatives, and mixtures thereof; and d) wherein said second part does not contain any oxidant wherein said oxidant comprises hypochlorite, chlorite, chlorate, perchlorate, N-halo compound, chlorine dioxide, peracid, peroxide, peroxygen bleach and mixtures thereof.

In accordance with the above objects and those that will be mentioned and will become apparent below, another aspect of the present invention comprises a solid-layered bleach composition having at least two parts comprising a first part part a second part: wherein said first part consisting essentially of a) 0.001%-50% of a hypochlorite selected from the group consisting of calcium hypochlorite, magnesium hypochlorite and mixtures thereof; b) a builder selected from the group consisting of carbonate, bicarbonate, sesquicarbonate and mixtures thereof; c) a water-soluble polymer selected from the group consisting of a polycarboxylate, sulfonated carboxylate, polysulfonate, polyvinylpyrrolidone, polyquaternary ammonium salts, copolymers and mixtures thereof; d) an acid selected from the group consisting of sulfonic acid, polysulfonic acid, carboxylic acid, dicarboxylic acid, polycarboxylic acid, acid sulfate, acid phosphate, phosphonic acid, and mixtures thereof; e) optionally a filler selected from die group consisting of chloride, sulfate, phosphate, silicate, borate, nitrate, chlorate, aluminate, silica-aluminate, hydroxide, and oxide compounds of alkali, metals, alkaline earths, aluminum, zinc and tin including hydrates, mono, di and tribasic compounds, mixed salts, borates, clays, zeolites and mixtures thereof; f) optionally, a water-swellable polymer selected from the group consisting of cross-linked polycarboxylate, cross-linked polysulfonate, cross-linked carboxymethyl cellulose, cellulose, sodium carboxymethylcellulose, and mixtures thereof; g) optionally, desiccants, solid processing aids, colorants, agglomeration aids, binders, glidants, corrosion inhibitors, and mixtures thereof; and h) wherein said first part does not contain sodium hypochlorite, lithium hypochlorite, potassium hypochlorite, sodium chlorite, chlorine dioxide, N-halogenated compounds, hydantoins, isocyanurates, carboxylic acids that also have hydroxyl, amino, amido, imino, or imido groups, enzymes, and mixtures thereof; and wherein the second part consisting essentially of, a) a functional ingredient selected from the group consisting of a surfactant, a hydrotrope, a wetting agent, a dispersant, a penetrant, a chelating agent, an odor absorbent, a fragrance, a flavoring agent, a sweetener, a colorant, a corrosion inhibitor, a viscosity modifier, a foam booster, a defoamer, a stain and soil repellant, a fluorescent whitening agent, an enzyme, a cloud point modifier, an anti-microbial agent, a sporulation agent, a catalyst, an activating agent, a therapeutic agent and mixtures thereof; b) a builder or filler selected from the group consisting of a carbonate, a bicarbonate, a sesquicarbonate, a chloride, a sulfate, a phosphate, a silicate, borate, a nitrate, an aluminate, a silica-aluminate, a hydroxide, or an oxide compound of alkali metals, alkaline earths, aluminum, zinc and tin including hydrates, mono, di and tribasic compounds, mixed salts, a borate, a clay, a zeolite, and mixtures thereof; c) optionally, a water-soluble polymer selected from the group consisting of a polycarboxylate, sulfonated carboxylate, polysulfonate, polyvinylpyrrolidone, polyquaternary ammonium salts, copolymers and mixtures thereof; d) optionally, an acid selected from the group consisting of sulfonic acid, polysulfonic acid, carboxylic acid, dicarboxylic acid, polycarboxylic acid, acid sulfate, acid phosphate, phosphonic acid, and mixtures thereof; e) optionally, a water-swellable polymer selected from the group consisting of cross-linked polycarboxylate, cross-linked polysulfonate, cross-linked carboxymethyl cellulose, cellulose, sodium carboxymethylcellulose, and mixtures thereof; f) optionally, desiccants, solid processing aids, colorants, agglomeration aids, binders, glidants, corrosion inhibitors, and mixtures thereof; and g) wherein said second part does not contain any oxidant wherein said oxidant comprises hypochlorite, chlorite, chlorate, perchlorate, N-halo compound, chlorine dioxide, peracid, peroxide, peroxygen bleach and mixtures thereof.

In accordance with the above objects and those that will be mentioned and will become apparent below, another aspect of the present invention comprising a solid-layered bleach composition having at least two parts comprising a first part and a second part: wherein said first part consisting of, a) 0.001%-50% of a hypochlorite selected from the group consisting of calcium hypochlorite, magnesium hypochlorite and mixtures thereof; b) a builder selected from the group consisting of carbonate, bicarbonate, sesquicarbonate and mixtures thereof; c) a water-soluble polymer selected from the group consisting of a polycarboxylate, sulfonated carboxylase, polysulfonate, polyvinylpyrrolidone, polyquaternary ammonium salts, copolymers and mixtures thereof; d) an acid selected from the group consisting of sulfonic acid, polysulfonic acid, carboxylic acid, dicarboxylic acid, polycarboxylic acid, acid sulfate, acid phosphate, phosphonic acid, and mixtures thereof; e) optionally a filler selected from the group consisting of chloride, sulfate, phosphate, silicate, borate, nitrate, chlorate, aluminate, silica-aluminate, hydroxide, and oxide compounds of alkali, metals, alkaline earths, aluminum, zinc and tin including hydrates, mono, di and tribasic compounds, mixed salts, borates, clays, zeolites and mixtures thereof; f) optionally, a water-swellable polymer selected from the group consisting of cross-linked polycarboxylate, cross-linked polysulfonate, cross-linked carboxymethyl cellulose, cellulose, sodium carboxymethylcellulose, and mixtures thereof; g) optionally, desiccants, solid processing aids, colorants, agglomeration aids, binders, glidants, corrosion inhibitors, and mixtures thereof; and h) wherein said first part does not contain sodium hypochlorite, lithium hypochlorite, potassium hypochlorite, sodium chlorite, chlorine dioxide, N-halogenated compounds, hydantoins, isocyanurates, carboxylic acids that also have hydroxyl, amino, amido, imino, or imido groups, enzymes, and mixtures thereof; and wherein said second part consisting of, a) a functional ingredient selected from the group consisting of a surfactant, a hydrotrope, a wetting agent, a dispersant, a penetrant, a chelating agent, an odor absorbent, a fragrance, a flavoring agent, a sweetener, a colorant, a corrosion inhibitor, a viscosity modifier, a foam booster, a defoamer, a stain and soil repellant, a fluorescent whitening agent, an enzyme, a cloud point modifier, an anti-microbial agent, a sporulation agent, a catalyst or an activating agent a therapeutic agent, and mixtures thereof; b) a builder or filler selected from the group consisting of a carbonate, a bicarbonate, a sesquicarbonate, a chloride, a sulfate, a phosphate, a silicate, borate, a nitrate, an aluminate, a silica-aluminate, a hydroxide, or an oxide compound of alkali metals, alkaline earths, aluminum, zinc and tin including hydrates, mono, di and tribasic compounds, mixed salts, a borate, a clay, a zeolite, and mixtures thereof; c) optionally, a water-soluble polymer selected from the group consisting of a polycarboxylate, sulfonated carboxylate, polysulfonate, polyvinylpyrrolidone, polyquaternary ammonium salts, copolymers and mixtures thereof; d) optionally, an acid selected from the group consisting of sulfonic acid, polysulfonic acid, carboxylic acid, dicarboxylic acid, polycarboxylic acid, acid sulfate, acid phosphate, phosphonic acid, and mixtures thereof; e) optionally, a water-swellable polymer selected from the group consisting of cross-linked polycarboxylate, cross-linked polysulfonate, cross-linked carboxymethyl cellulose, cellulose, sodium carboxymethylcellulose, and mixtures thereof; f) optionally, desiccants, solid processing aids, colorants, agglomeration aids, binders, glidants, corrosion inhibitors, and mixtures thereof; and g) wherein said second part does not contain any oxidant wherein said oxidant comprises hypochlorite, chlorite, chlorate, perchlorate, N-halo compound, chlorine dioxide, peracid, peroxide, peroxygen bleach, and mixtures thereof.

Further features and advantages of the present invention will become apparent to those of ordinary skill in the art in view of the detailed description of preferred embodiments below, when considered together with the attached claims.

DETAILED DESCRIPTION OF THE INVENTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("%'s") are in weight percent (based on 100% active) of the cleaning composition alone, not accounting for the substrate weight. Each of the noted cleaner composition components and substrates is discussed in detail below. Additionally, this application also covers method and method of use steps of utilizing the compositions described in the present invention.

The term "comprising", which is synonymous with "including," "containing," or "characterized by," is inclusive or open-ended and does not exclude additional, unrecited elements or method steps. See MPEP 2111.03. See, e.g., *Mars Inc.* v. *H.J. Heinz Co.*, 377 F.3d 1369, 1376, 71 USPQ2d 1837, 1843 (Fed. Cir. 2004) ("like the term 'comprising' the terms 'containing' and 'mixture' are open-ended."), *Invitrogen Corp.* v. *Biocrest Mfg., L.P.*, 327 F.3d 1364, 1308, 66 USPQ2d 1631, 1634 (Fed. Cir. 2003) ("The transition 'comprising' in a method claim indicates that the claim is open-ended and allows for additional steps,"); *Genentech, Inc.* v. *Chiron Corp.*, 112 F.3d 495, 501, 42 USPQ2d 1608, 1613 (Fed. Cir. 1997) See MPEP 2111.03. ("Comprising" is a term of art used in claim language which means that the named elements are essential, hut other elements may be added and still form a construct within the scope of the claim.); *Moleculon Research Corp.* v. *CBS, Inc.*, 793 F.2d 1261, 229 USPQ 805 (Fed. Cir. 1986); *In re Baxter*, 656 F.2d 679, 686, 210 USPQ 795, 803 (CCPA 1981); *Ex parte Davis*. 80 USPQ 448, 450 (Bd. App. 1948). See MPEP 2111.03.

The term "consisting essentially of" as used herein, limits the scope of a claim to the specified materials or steps "and those that do not materially affect the basic and novel characteristic(s)" of the claimed invention. *In re Herz*, 537 F.2d 549, 551-52, 190 USPQ 461, 463 (CCPA 1976) (emphasis in original). See MPEP 2111.03.

The term "consisting of" as used herein, excludes any element, step, or ingredient not specified in the claim. In re Gray 53 F.2d 520, 11 USPQ 255 (CCPA 1931); Ex Parte Davis, 80 USPQ 448, 450 (Bd. App. 1948). See MPEP 2111.03.

The term "cleaning composition", as used herein, is meant to mean and include a cleaning formulation having at least one surfactant.

The terms "laundry composition", as used herein, is meant to mean and include a laundry formulation having at least one surfactant.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes anionic, nonionic, cationic, zwiterrionic, amphoteric agents or mixtures thereof.

General

The present invention is directed to a solid-layered composition comprising at least two parts. The solid-layered composition may optionally have a third part. If a third part is present, the third part is situated between the first and second parts. The present invention does not work with a liquid composition. The first part of the solid-layered composition comprises at least calcium hypochlorite, magnesium hypochlorite or mixtures thereof. The second part of the solid-layered composition comprises at least one functional ingredient. Optional ingredients may be added to either part to enhance the efficacy of the solid-layered composition.

Oxidant

The first part of the solid-layered composition can contain only calcium hypochlorite, magnesium hypochlorite or mixtures thereof. The first part of the solid-layered composition does not contain any other types of hypochlorite such as sodium hypochlorite, lithium hypochlorite, or potassium hypochorite. Therefore, the first part of the solid-layered composition does not contain any of the following compounds: hypobromites, hypoiodites, chlorinated trisodium phosphate dodecahydrates, potassium and sodium dichloroisocyanurates, trichlorocyanuric acid, N-chloroimides, N-chloroamides, N-chlorosulfamide, N-chloroamines, chlorohydantoins such as dichlorodimethyl hydantoin and chlorobromo dimethylhydantoin, bromo-compounds corresponding to the chloro-compounds above. The first part of the composition preferably does not contain compounds that form or release chlorine dioxide such as sodium chlorite. Preferably the first part of the composition also does not contain an oxygen bleach, peroxygen, peroxyhydrate or active oxygen generating compound as described in the following section.

The second part of the solid-layered composition does not contain any oxidant. Oxidants, when used, include, but are not limited to, hypohalite (including any hypochlorite species), peracids, N-halo compound, hydrogen peroxide, and/or sources of hydrogen peroxide. Therefore, the second part of the solid-layered composition cannot contain an oxygen bleach, including a peroxygen, peroxyhydrate or active oxygen generating compound. As used herein a source of hydrogen peroxide refers to any compound which generates active oxygen when said compound is in contact with water. Therefore, the second part of the solid-layered composition cannot contain percarbonates, perborates, preformed percarboxylic acids, persilicates, persulphates, organic and inorganic peroxides and/or hydroperoxides. Additionally, the second part of the solid-layered composition does not contain the following compounds; hypochlorites, hypobromites, hypoiodites, hypochlorous, acids, chlorinated trisodium phosphate dodecahydrates, potassium and sodium dichloroisocyanurates, trichloro-cyanuric acid, N-chloroimides, N-chloroamides, N-chlorosulfamide, N-chloroamines, chlorohydantoins such as dichlorodimethyl hydantoin and chlorobromo dimethylhy-dantoin, bromo-compounds corresponding to the chloro-compounds above.

The compositions of the present invention do not comprise a peroxygen bleach activator. By "peroxygen bleach activator", it is meant herein a compound which reacts with peroxygen bleach like hydrogen peroxide to form a peracid. The peracid thus formed constitutes the activated bleach. Bleach activators that are not to be used in the composition include, but are not limited to, those belonging to the class of esters, amides, imides, or anhydrides. Examples of bleach activators that are not to be used in the composition include, but are not limited to, TAED, sodium 3,5,5 trimethyl hexanoyloxy-benzene sulphonate, diperoxy dodecanoic acid, nonylamide of peroxyadipic acid, nonylamide of peroxyadipic acid, n-nonanoyloxybenzenesulfonate (NOBS), acetyl triethyl citrate (ATC), n-alkyl alkyl ammonium acetonitrile activators. Examples of bleach activators that are not to be used in the composition include, but are not limited to, are N-acyl caprolactams selected from the group consisting of substituted or unsubstituted benzoyl caprolactam, octanoyl caprolactam, nonanoyl caprolactam, hexanoyl caprolactam, decanoyl caprolactam, undecenoyl caprolactam, formyl caprolactam, acetyl caprolactam, propanoyl caprolactam, butanoyl caprolactam pentanoyl caprolactam or mixtures thereof.

Suitably, the calcium hypochlorite, magnesiusn hypochlorite and mixtures thereof in the first part of the solid-layered composition is present in the composition in an amount ranging from about 0.001% to about 50%, about 0.001% to about 45%, about 0.001% to about 40%, about 0.001% to about 30%, about 0.001% to about 25%, about 0.001% to about 20%, about 0.001% to about 15%, about 0.001% to about 10%, about 0.001% to about 5%, about 5% to about 20%, about 5% to about 15%, about 10% to about 20%, about 10% to about 15% and about 15% to about 20%.

Builder

The composition can contain a builder. In one embodiment, the first and second part of the solid-layered composition can contain a builder. In another embodiment, the first part of the solid-layered composition only contains a builder. In another embodiment, the second part of the solid-layered composition only contains a builder. Suitably, the builder is present in the cleaning composition in an amount ranging from about 10% to about 90%, about 20% to about 90%, about 20% to about 80%, about 20% to about 60%, about 20% to about 50%, about 30% to about 60%, about 35 to about 55%, about 40 to about 50%, about 20% to about 30% to 55%, about 30% to about 50%, about 30% to about 45%, about 30% to about 40%, about 20% to about 60%, about 25% to about 60%, about 20% to about 40%, about 20% to about 30%. The builder can be selected from inorganic builders, such as alkali metal carbonate, alkali metal bicarbonate, alkali metal hydroxide, alkali metal silicate and combinations thereof.

The composition can include a builder, which can increase the effectiveness of the surfactant. The builder can also function as a softener, a sequestering agent, a buffering agent, or a pH adjusting agent in the cleaning composition. A variety of builders or buffers can be used and they include, but are not limited to, phosphate-silicate compounds, zeolites, alkali metal, ammonium and substituted ammonium polyacetates, trialkali salts of nitrilotriacetic acid, carboxylases, polycarboxylates, carbonates, bicarbonates, polyphosphates, aminopolycarboxylates, polyhydroxy-sulfonates, and starch derivatives. Builders, when used, include, but are not limited to, organic acids, mineral acids, alkali metal and alkaline earth salts of silicate, metasilicate, polysilicate, borate, sulfates, hydroxide, carbonate, carbamate, phosphate, polyphosphate, pyrophosphates, triphosphates, tetraphosphates, ammonia, hydroxide, monoethanolamine, monopropanolamine, diethanolamine, dipropanol-amine, triethanolamine, and 2-amino-2methylpropanol. Other suitable buffers include ammonium carbamate, citric acid, and acetic acid. Mixtures of any of the above are also acceptable. Useful inorganic buffers/alkalinity sources include, but are not limited to, ammonia, the alkali metal carbonates and alkali metal phosphates, e.g., sodium carbonate, sodium polyphosphate. For additional buffers see WO 95/07971, which is incorporated herein by reference. Other preferred pH adjusting agents include sodium or potassium hydroxide. The term silicate is meant to encompass silicate, metasilicate, polysilicate, aluminosilicate and similar compounds. Preferred buffers for both first and second parts of the solid-layered composition include carbonate, bicarbonate, sesquicarbonate and mixtures thereof.

Water-Soluble Polymer

The composition can contain a water-soluble polymer. In one embodiment, the first part of the solid-layered composition can contain a water-soluble polymer. In another embodiment, the second part of the solid-layered composition can contain a water-soluble polymer. In another embodiment, the first and second parts of the solid-layered composition can contain a water-soluble polymer. Examples of water-soluble polymer include, but are not limited to, polycarboxylate, sulfonated carboxylate, polysulfonate, polyvinylpyrrolidone ("PVP"), and mixtures thereof.

Examples of polycarboxylate include, but are not limited to, polymers with sufficient carboxylate ions to achieve water solubility. Carboxylate ions may be derived from various monomers including acrylic acid, maleic acid and maleic anhydride. Copolymers of different carboxylate-containing monomers are also suitable as well as copolymers with non carboxylate containing monomers such as methacrylate, acrylonitrile, styrene, ethylene, propylene, and many others. Mixtures of carboxylate containing polymers can also be used.

Suitably, the molecular weight of the water-soluble polymer may be between about 1,000 to about 10,000 daltons, about 1,000 to about 8,000 daltons, about 1,000 to about 6,000 daltons, about 1,000 to about 5,000 daltons, about 1,000 to about 4,000 daltons, about 1000 to about 2,000 daltons, about 2,000 to about 10,000 daltons, about 2,000 to about 8,000 daltons, about 2,000 to about 6,000 daltons, about 2,000 to about 5,000 daltons, about 2,000 to about 4,000 daltons, about 3,000 to about 10,000 daltons, about 3,000 to about 8,000 daltons, about 3,000 to about 6,000 daltons, about 3,000 to about 5,000 daltons, about 3,000 to about 5,000 daltons, about 4,000 to about 10,000 daltons, about 4,000 to about 8,000 daltons, about 4,000 to about 6,000 daltons, about 5,000 to about 10,000 daltons, about 5,000 to about 7,500 daltons, and about 7,500 to about 10,000 daltons.

Suitably, the water-soluble polymer is present in an amount ranging from: about 0.1% to about 60%, about 0.1% to about 50%, about 0.1% to about 40%, about 0.1% to about 30%, about 0.1% to about 20%, about 0.1% to about 15%, about 0.1% to about 10%, about 5% to about 60%, about 5% to about 50%, about 5% to about 40%, about 5% to about 30%, about 5% to about 20%, about 5% to about 10%, about 10% to about 60%, about 10% to about 50%, about 10% to about 40%, about 10% to about 30%, about 10% to 20%, about 20% to about 60%, about 20% to about 50%, about 20% to about 40%, about 20% to about 30%, about 30% to about 60%, about 30% to about 50%, about 30% to about 40%, about 40% to about 60%.

Filler

The composition may also optionally contain a filler. In one embodiment, all parts of the solid-layered composition comprise a filler. In another embodiment, the first part of the solid-layered composition only comprises a filler. In another embodiment, the second part of the solid-layered composition only comprises a filler. In another embodiment, a third part of the solid-layered composition only comprises a filler. Examples of fillers that can be used with the present invention include, but are not limited to, a carbonate, a bicarbonate, a sesquicarbonate, a chloride, a sulfate, a phosphate, a silicate, borate, a nitrate, an aluminate, a silica-aluminate, a hydroxide, or an oxide compound of alkali metals, alkaline earths, aluminum, zinc and tin including hydrates, mono, di and tribasic compounds, mixed salts, a borate, a clay, a zeolite, and mixtures thereof. Specific examples of fillers include, but are not limited to, sodium carbonate, potassium carbonate, zinc carbonate, calcium carbonate, magnesium carbonate, sodium bicarbonate, potassium bicarbonate, magnesium bicarbonate, sodium sesquicarbonate, sodium chloride, sodium sulfate, zinc sulfate, magnesium sulfate, calcium sulfate, sodium phosphate, sodium aluminum phosphate, disodium hydrogen phosphate, sodium dihydrogen phosphate, nesosilicates, sorosilicates, cyclosilicates, inosilicates (single or double chain), phyllosilicates, tectosilicates, sodium silicate, borax, boric acid, diborates, triborates, tetraborates, metaborates, sodium nitrate, potassium nitrate, calcium nitrate, magnesium nitrate, sodium aluminate, potassion aluminate, tricalcium aluminate, alumina oxide, magnesium oxide, aluminum hydroxide, calcium hydroxide, magnesium hydroxide, calcium hydroxide, calcium oxide, zinc oxide, tin dioxide, titanium dioxide, silica alumina, and zeolite A.

Acid

The composition can contain an acid. In one embodiment, both parts of the solid-layered composition comprise an acid. In another embodiment, the first part of the solid-layered composition only comprises an acid. In another embodiment, the second part of the solid-layered composition only comprises an acid. Examples of acids that can be used with the present invention include, but are limited to, sulfonic acid, polysulfonic acid, carboxylic acid, polycarboxylic acid, acid sulfate, acid phosphate, phosphonic acid, dicarboxylic acid, monocarboxylic acid, aminocarboxylic acid and mixtures thereof. Specific examples of acids, include but are not limited to, succinic acid, adipic acid, sodium bisulfate, glutaric acid, 3-pyridine sulfonic acid, dodecyl benzene sulfonic acid, polyacrylic acid, and mixtures thereof.

The first part of the composition does not contain carboxylic acids that have one or more hydroxyl group moieties. Examples of acids that are not to be used in the composition include, but are not limited to, citric acid, tartaric acid. The first part of the composition also does not contain aliphatic or aromatic amines that possess a covalently bound proton to the nitrogen moiety. Examples of acids that are not to be used in the composition include, but are not limited to alanine.

Suitably, the acid is present in an amount ranging from about 0.1% to about 50%, about 0.1% to about 40%, about 0.1% to about 30%, about 0.1% to about 20%, about 0.1% to about 15%, about 0.1% to about 10%, about 5% to about 50%, about 5% to about 40%, about 5% to about 30%, about 5% to about 20%, about 5% to about 10%, about 10% to about 50%, about 10% to about 40%, about 10% to about 30%, about 10% to 20%, about 20% to about 50%, about 20% to about 40%, about 20% to about 30%, about 30% to about 50%, about 30% to about 40%, about 40% to about 50%.

Cross-Linked Water-Swellable Polymer

The composition may optionally contain a cross-linked water-swellable polymer. In one embodiment, the first part of the solid-layered composition only contains a cross-linked water-swellable polymer. In another embodiment the second part of the solid-layered composition only contains a cross-linked water-swellable polymer. In another embodiment, the first and second parts of the solid-layered composition contain a cross-linked water-swellable polymer. Examples of water-swellable polymer include, but are not limited to, cross-linked polycarboxylate, cross-linked polysulfonate, cross-linked carboxymethylcellulose, cross-linked PVP, cross-linked carboxymethyl cellulose, cellulose, sodium carboxymethylcellulose and mixtures thereof.

Suitably, the molecular weight of the water-swellable polymer may be between about 1,000 to about 10,000 daltons, about 1,000 to about 8,000 daltons, about 1,000 to about 6,000 daltons, about 1,000 to about 5,000 daltons, about 1,000 to about 4,000 daltons, about 1,000 to about 2,000 daltons, about 2,000 to about 10,000 daltons, about 2,000 to about 8,000 daltons, about 2,000 to about 6,000 daltons, about 2,000 to about 5,000 daltons, about 2,000 to about 4,000 daltons, about 3,000 to about 10,000 daltons, about 3,000 to about 8,000 daltons, about 3,000 to about 6,000 daltons, about 3,000 to about 5,000 daltons, about 3,000 to about 5,000 daltons, about 4,000 to about 10,000 daltons, about 4,000 to about 8,000 daltons, about 4,000 to about 6,000 daltons, about 5,000 to about 10,000 daltons, about 5,000 to about 7,500 daltons, and about 7,500 to about 10,000 daltons.

Suitably, the water-swellable polymer is optionally present in an amount ranging from about 0.1% to about 60%, about 0.1% to about 50%, about 0.1% to about 40%, about 0.1% to about 30%, about 0.1% to about 20%, about 0.1% to about 15%, about 0.1% to about 10%, about 5% to about 60%, about 5% to about 50%, about 5% to about 40%, about 5% to about 30%, about 5% to about 20%, about 5% to about 10%, about 10% to about 60%, about 10% to about 50%, about 10% to about 40%, about 10% to about 30%, about 10% to 20%, about 20% to about 60%, about 20% to about 50%, about 20% to about 40%, about 20% to about 30%, about 30% to about 60%, about 30% to about 50%, about 30% to about 40%, about 40% to about 60%.

Functional Ingredients

Functional ingredients are included in the compositions to provide a pleasant fragrance, improve soil removal, increase wetting, inhibit corrosion, or provide other desirable benefits. Example of functional ingredients include, but are not limited to, surfactants, hydrotropes, wetting agents, penetrants, chelating agents, odor masking agents, odor absorbing agents, colorants, fluorescent whitening agents, flavoring agents, sweeteners, catalysts, potentiators, activating agents, anti-microbial compounds, sporulation agents, corrosion inhibitors, therapeutic agents, viscosity modifiers, and foam stabilizers. In one embodiment, one functional ingredient may be used. More than one functional ingredient may be included to provide multiple benefits. In another embodiment the functional ingredient may be in the second part of the composition (i.e., hypochlorite would be in the first part) In some cases combinations of different types of functional ingredients may be preferred. For example including an odor absorbing agent with an odor masking agent or fragrance may provide better odor control than when only one of these ingredients are present. In another example combining surfactants with hydrotropes or wetting agents may synergistically enhance cleaning or antimicrobial properties. The functional ingredients may be present in the second part at a level of from about 0.1% to about 99%, or from about 0.1% to about 80%, or from about 0.1% to about 60%, or from about 0.1% to about 40%, or from about 0.1% to about 20%, or from about 0.1% to about 15% or from about 0.1% to about 10% or from about 0.1% to about 5% or from about 0.1% to about 1%, or from about 0.01% to about 1%, or from about 5% to about 50%, or from about 5% to about 25% or from about 5% to about 15%, or from about 5% to about 10%, or from about 10% to about 60%, or from about 10% to about 40%, or from about 10% to about 20%, or from about 20% to about 60%, or about 20% to about 40%, or about 15% to about 25%.

Surfactant

The composition may contain one or more surfactants selected from nonionic, anionic, cationic, ampholytic, amphoteric and zwitterionic surfactants and mixtures thereof. Preferably, the surfactant is present in the second part of the solid-layered composition. A typical listing of anionic, ampholytic, and zwitterionic classes, and species of these surfactants, is given in U.S. Pat. No. 3,029,678 to Laughlin and Heuring. A list of suitable cationic surfactants is given in U.S. Pat. No. 4,259,217 to Murphy.

The composition may comprise an anionic surfactant. Essentially any anionic surfactants useful for detersive purposes can be used in the cleaning composition. These can include salts (including, for example, sodium, potassium, ammonium, and substituted ammonium salts such as mono-, di- and tri-ethanolamine salts) of the anionic sulfate, sulfonate, carboxylate and sarcosinate surfactants. Anionic surfactants may comprise a sulfonate or a sulfate surfactant. Anionic surfactants may comprise an alkyl sulfate, a linear or branched alkyl benzene sulfonate, or an alkyldiphenyloxide disulfonate, as described herein.

Other anionic surfactants include the isethionates such as the acyl isethionates, N-acyl taurates, fatty acid amides of methyl tauride, alkyl succinates and sulfosuccinates, monoesters of sulfosuccinate (for instance, saturated and unsaturated C12-C18 monoesters) diesters of sulfosuccinate (for instance saturated and unsaturated C6-C14 diesters), N-acyl sarcosinates. Resin acids and hydrogenated resin acids are also suitable, such as rosin, hydrogenated rosin, and resin acids and hydrogenated resin acids present in or derived from tallow oil. Anionic sulfate surfactants suitable for use herein include the linear and branched primary and secondary alkyl sulfates, alkyl ethoxysulfates, fatty oleoyl glycerol sulfates, alkyl phenol ethylene oxide ether sulfates, the C5-C17acyl-N—(C1-C4 alkyl) and —N—(C1-C2 hydroxyalkyl) glucamine sulfates, and sulfates of alkylpolysaccharides such as the sulfates of alkylpolyglucoside (the nonionic nonsulfated compounds being described herein). Alkyl sulfate surfactants may be selected from the linear and branched primary C10-C18 alkyl sulfates, the C11-C15 branched chain alkyl sulfates, or the C12-C14 linear chain alkyl sulfates.

Alkyl ethoxysulfate surfactants may be selected from the group consisting of the C10-C18 alkyl sulfates, which have been ethoxylated with from 0.5 to 20 moles of ethylene oxide per molecule. The alkyl ethoxysulfate surfactant may be a C11-C18, or a C11-C15 alkyl sulfate which has been ethoxylated with from 0.5 to 7, or from 1 to 5, moles of ethylene oxide per molecule. One aspect of the invention employs mixtures of the alkyl sulfate and/or sulfonate and alkyl ethoxysulfate surfactants. Such mixtures have been disclosed in PCT Patent Application No. WO 93/18124.

Anionic sulfonate surfactants suitable for use herein include the salts of C5-C20 linear alkylbenzene sulfonates, alkyl ester sulfonates, C6-C22 primary or secondary alkane sulfonates, C6-C24 olefin sulfonates, sulfonated polycarboxylic acids, alkyl glycerol sulfonates, fatty acyl glycerol sulfonates, fatty oleyl glycerol sulfonates, and any mixtures thereof. Suitable anionic carboxylate surfactants include the alkyl ethoxy carboxylases, me alkyl polyethoxy polycarboxylate surfactants and the soaps ('alkyl carboxyls'), especially certain secondary soaps as described herein. Suitable alkyl ethoxy carboxylases include those with the formula

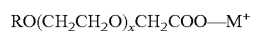
$RO(CH_2CH_2O)_xCH_2COO—M^+$ wherein R is a C6 to C18 alkyl group, x ranges from 0 to 10, and the ethoxylate distribution is such that, on a weight basis, the amount of material where x is 0 is less than 20% and M is a cation. Suitable alkyl polyethoxypolycarboxylate surfactants include those having the formula $RO—(CHR^1—CHR^2—O)—R^3$ wherein R is a C6 to C18 alkyl group, x is from 1 to 25, $R^1$ and $R^2$ are selected from the group consisting of hydrogen, methyl acid radical, succinic acid radical, hydroxysuccinic acid radical and mixtures thereof, and $R^3$ is selected from the group consisting of hydrogen, substituted or nonsubstituted hydrocarbon having between 1 and 8 carbon atoms, and mixtures thereof.

Suitable soap surfactants include the secondary soap surfactants, which contain a carboxyl unit connected to a secondary carbon. Suitable secondary soap surfactants for use heroin are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid and 2-pentyl-1-heptanoic acid. Certain soaps may also be included as suds suppressors.

Other suitable anionic surfactants are the alkali metal sarcosinates of formula R—CON ($R^1$) CH—)COOM, wherein R is a C5-C17 linear or branched alkyl or alkenyl group, $R^1$ is a C1-C4 alkyl group and M is an alkali metal ion. Examples are the myristyl and oleoyl methyl sarcosinates in the form of their sodium salts.

Other suitable surfactants include fatty acid sarosinates which are mild, biodegradable anionic surfactants derived from fatty acids and sarcosine (amino acid). Sarcosine is the N-methyl derivative of glycine. Sarcosine is a natural amino acid found in muscles and other tissues. Sarcosine is found naturally as an intermediate in the metabolism of choline to glycine. In a preferred embodiment, the sarcosines are acyl sarcosines. Examples of acyl sarcosines include, but are not limited to, cocoyl sarcosine, lauroyl sarcosine, myristoyl sarcosine, oleoyl sarcosine, stearoyl sarcosine which are modified fatty acids. The salts of acyl sarcosines are referred to acyl sarcosinates. Acyl sarcosinates useful herein include, for example, those having a formula:

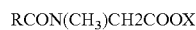
$RCON(CH_3)CH2COOX$ wherein R is an alkyl or alkenyl having from 8 to 22 carbon atoms, preferably from 12 to 18 carbon atoms, more preferably from 12 to 14 carbon atoms; and X is a sodium, potassium, ammonium, or triethanolamine.

Examples of acyl sarcosinates that can be used with the present invention include, but not limited to, sodium coccyl sarcosinate, sodium lauroyl sarcosinate and sodium myristoyl sarcosinate, sodium oleoyl sarcosinate, sodium stearoyl sarcosinate, ammonium coccyl sarcosinate, ammonium lauroyl sarcosinate and ammonium myristoyl sarcosinate, ammounium oleoyl sarcosinate and ammonium stearoyl sarcosinate. Commercially available preferred acyl sarcosinates include, but are not limited to, for example, sodium lauroyl sarcosinate having the tradename Hamposyl® L30 which is available from Hampshire Chemicals, and sodium cocoyl sarcosinate having the tradename Hamposyl® C30 which is available from Hampshire Chemicals.

Other suitable surfactants include fatty alcohol sulfate which has a higher alcohol or alkyl group is normally in the range of 10 to 18 carbon atoms. The cation will almost invariably be sodium or will include sodium, although other cations, such as triethanolamine, potassium, ammonium, magnesium and calcium. Preferred fatty alcohol sulfates are those wherein the fatty alcohol is essentially saturated and is of carbon content(s) within the 10 to 18 carbon atoms range, preferably 10 or 12 to 14 or 16 carbon atoms, such as 12 to 16, or that is derived from coconut oil (coco), palm oil, or palm kernel oil. Lauryl sulfates, and particularly, sodium lauryl sulfate, are preferred primary detergents but such designation also may apply to such detergents wherein the carbon chain length of the alcohol is not limited to 12 carbon atoms, but is primarily (over 50% and normally over 70 or 75%) of 12 to 14 carbon atoms. Such materials may be obtained from natural sources, such as coconut oil and palm kernel oil. In one embodiment, the fatty alcohol sulfate is a C12-C18 fatty alcohol sulfate. In another embodiment the fatty alcohol sulfate is a C12-C16 fatty alcohol sulfate. In another embodiment, the fatty alcohol sulfate is a C12-C14 fatty alcohol sulfate. In another embodiment, the fatty alcohol is a C12 fatty alcohol sulfate. In another embodiment, the fatty alcohol sulfate is sodium lauryl sulfate. In a specific embodiment, the fatty alcohol sulfate is a sodium coco fatty alcohol sulfate.

Suitable amphoteric surfactants for use herein include the amine oxide surfactants and the alkyl amphocarboxylic acids. Suitable amine oxides include those compounds having the formula $R^3(OR^4)_xNO(R^5)_2$ wherein $R^3$ is selected from an alkyl, hydroxyalkyl, acylamidopropyl and alkylphenyl group, or mixtures thereof, containing from 8 to 26 carbon atoms; $R^4$ is an alkylene or hydroxyalkylene group containing from 2 to 3 carbon atoms, or mixtures thereof, x is from 0 to 5, preferably from 0 to 3; and each $R^5$ is an alkyl or hydroxyalkyl group containing from 1 to 3, or a polyethylene oxide group containing from 1 to 3 ethylene oxide groups. Suitable amine oxides are C10-C18 alkyl dimethylamine oxide, and C10-18 acylamido alkyl dimethylamine oxide. A suitable example of an alkyl amphodicarboxylic acid is Miranol™ C2M Conc. manufactured by Miranol, Inc., Dayton, N.J.

Zwitterionic surfactants can also be incorporated into the cleaning compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. Betaine and sultaine surfactants are exemplary zwittenionic surfactants for use herein.

Suitable betaines are those compounds having the formula $R(R^1)_2N^+R^2COO^-$ wherein R is a C6-C18 hydrocarbyl group, each $R^1$ is typically C1-C3 alkyl and $R^2$ is a C1-C5 hydrocarbyl group. Suitable betaines are C12-C18 dimethylammonio hexanoate and the C10-18 acylamidopropane (or ethane) dimethyl (or diethyl) betaines. Complex betaine surfactants are also suitable for use herein.

Suitable cationic surfactants to be used herein include the quaternary ammonium surfactants. The quaternary ammonium surfactant may be a mono C6-C16, or a C6-C10 N-alkyl or alkenyl ammonium surfactant wherein the remaining N positions are substituted by methyl, hydroxyethyl or hydroxypropyl groups. Suitable are also the mono-alkoxylated and bis-alkoxylated amine surfactants. Additional suitable cationic surfactants include coco fatty acid diethanolamine, hydrogenated palm tea ester quat and cationic ethyoxylate fatty acids.

Another suitable group of cationic surfactants, which can be used in the cleaning compositions, are cationic ester surfactants. The anionic ester surfactant is a compound having surfactant properties comprising at least one ester (i.e. —COO—) linkage and at least one cationically charged group. Suitable cationic ester surfactants, including choline ester surfactants, have for example been disclosed in U.S. Pat. Nos. 4,228,042, 4,239,660 and 4,260.520. The ester linkage and cationically charged group may be separated from each other in the surfactant molecule by a spacer group consisting of a chain comprising at least three atoms (i.e. of three atoms chain length), or from three to eight atoms, or from three to five atoms, or three atoms. The atoms forming the spacer group chain are selected from the group consisting, of carbon, nitrogen and oxygen atoms and any mixtures thereof, with the proviso that any nitrogen or oxygen atom in said chain connects only with carbon atoms in the chain. Thus spacer groups having, for example —O—O— (i.e. peroxide), —N—N—, and —N—O— linkages are excluded, whilst spacer groups having, for example —CH$_2$—O—, CH$_2$— and —CH$_2$—NH—CH$_2$— linkages are included. The spacer group chain may comprise only carbon atoms, or the chain is a hydrocarbyl chain.

The cleaning composition may comprise cationic monoalkoxylated amine surfactants, for instance, of the general formula: $R^1R^2R^3N^+ ApR^4 X^-$ wherein $R^1$ is an alkyl or alkenyl moiety containing from about 6 to about 18 carbon atoms, or from 6 to about 16 carbon atoms, or from about 6 to about 14 carbon atoms; $R^2$ and $R^3$ are each independently alkyl groups containing from one to about three carbon atoms, for instance, methyl, for instance, both $R^2$ and $R^3$ are methyl groups; $R^4$ is selected from hydrogen, methyl, and ethyl; $X^-$ is an anion such as chloride, bromide, methylsulfate, sulfate, or the like, to provide electrical neutrality; A is a alkoxy group, especially a ethoxy, propoxy or butoxy group; and p is from 0 to about 30, or from 2 to about 15, or from 2 to about 8. The $ApR^4$ group in the formula may have p=1 and is a hydroxyalkyl group, having no greater than 6 carbon atoms whereby the —OH group Is separated from the quaternary ammonium nitrogen atom by no more than 3 carbon atoms. Suitable $ApR^4$ groups are —CH$_2$CH$_2$—OH, —CH$_2$CH$_2$CH$_2$—OH, —CH$_2$CH(CH$_3$)—OH and —CH(CH$_3$)CH$_2$—OH. Suitable $R^1$ groups are linear alkyl groups, for instance, linear $R^1$ groups having from 8 to 14 carbon atoms.

Suitable cationic mono-alkoxylated amine surfactants for use herein are of the formula $R^1(CH_3)(CH_3)N^+(CH_2CH_2O)_{2-5}H X^-$ wherein $R^1$ is C10-C18 hydrocarbyl and mixtures thereof, especially C10-C14 alkyl, or C10 and C12 alkyl, and X is any convenient anion to provide charge balance, for instance, chloride or bromide.

As noted, compounds of the foregoing type include those wherein the ethoxy ($CH_2CH_2O$) units (EO) are replaced by butoxy, isopropoxy [$CH(CH_3)CH_2O$] and [$CH_2CH(CH_3)O$] units (i-Pr) or n-propoxy units (Pr), or mixtures of EO and/or Pr and/or i-Pr units.

The cationic bis-alkoxylated amine surfactant may have the general formula: $R^1R^2N^+ApR^3A'qR^4X^-$ wherein $R^1$ is an alkyl or alkenyl moiety containing from about 8 to about 18 carbon atoms, or from 10 to about 16 carbon atoms, or from about 10 to about 14 carbon atoms; $R^2$ is an alkyl group containing from one to three carbon atoms, for instance, methyl; $R^3$ and $R^4$ can vary independently and are selected from hydrogen, methyl and ethyl, $X^-$ is an anion such as chloride, bromide, methylsulfate, sulfate, or the like, sufficient to provide electrical neutrality, A and A' can vary independently and are each selected from C1-C4 alkoxy, for instance, ethoxy, (i.e., —$CH_2CH_2O$—), propoxy, butoxy and mixtures thereof, p is from 1 to about 30, or from 1 to about 4 and q is from 1 to about 30, or from 1 to about 4, or both p and q are 1.

Suitable cationic bis-alkoxylated amine surfactants for use herein, are of the formula $R^1CH_3N^+(CH_2CH_2OH)(CH_2CH_2OH) X^-$, wherein $R^1$ is C10-C18 hydrocarbyl and mixtures thereof of C10, C12, C14 alkyl and mixtures thereof, $X^-$ is any convenient anion to provide charge balance, for example, chloride. With reference to the general cationic bis-alkoxylated amine structure noted above, since in one example compound $R^1$ is derived from (coconut) C12-C14 alkyl fraction fatty acids, $R^2$ is methyl and $ApR^3$ and $A'qR^4$ are each monoethoxy.

Other cationic bis-alkoxylated amine surfactants useful herein include compounds of the formula: $R^1R^2N^+—(CH_2CH_2O)_pH—(CH_2CH_2O)_qH X^-$ wherein $R^1$ is C10-C18 hydrocarbyl, or C10-C14 alkyl, independently p is 1 to about 3 and q is 1 to about 3, $R^2$ is C1-C3 alkyl, for example, methyl, and $X^-$ is an anion, for example, chloride or bromide.

Other compounds of the foregoing type include those wherein the ethoxy ($CH_2CH_2O$) units (EO) are replaced by butoxy (Bu) isopropoxy [$CH(CH_3)CH_2O$] and [$CH_2CH(CH_3)O$] units (i-Pr) or n-propoxy units (Pr), or mixtures of EO and/or Pr and/or i-Pr units.

The inventive compositions may include at least one fluorosurfactant selected from nonionic fluorosurfactants, cationic fluorosurfactants, and mixtures thereof which are soluble or dispersible in the aqueous compositions being taught herein, sometimes compositions which do not include further detersive surfactants, or further organic solvents, or both. Suitable nonionic fluorosurfactant compounds are found among the materials presently commercially marketed under the tradename Fluorad® (ex. 3M Corp.) Exemplary fluorosurfactants include those sold as Fluorad® FC-740, generally described to be fluorinated alkyl esters; Fluorad® FC-430, generally described to be fluorinated alkyl esters; Fluorad® FC-431, generally described to be fluorinated alkyl esters; and, Fluorad® FC-170-C, which is generally described as being fluorinated alkyl polyoxyethlene ethanols.

An example of a suitable cationic fluorosurfactant compound has the following structure: $C_nF_{2n+1}SO_2NHC_3H_6N^+(CH_3)_3I^-$ where n~8. This cationic fluorosurfactant is available under the tradename Fluorad® FC-135 from 3M. Another example of a suitable cationic fluorosurfactant is $F_3$

wherein; n is 5-9 and m is 2, and $R_1$, $R_2$ and $R_3$ are —$CH_3$. This cationic fluorosurfactant is available under the tradename ZONYL® FSD (available from DuPont, described as 2-hydroxy-3-((gamma-omega-perfluoro-$C_{6-20}$-alkyl)thio)-N,N,N-trimethyl-1-propyl ammonium chloride). Other cationic fluorosurfactants suitable for use in the present invention are also described in EP 806,115 to Leach and Niwata. The fluorosurfactant selected from the group of nonionic fluorosurfactant, cationic fluorosurfactant, and mixtures thereof may be present in amounts of from 0.001 to 5% wt., preferably from 0.01 to 1% wt., and more preferably from 0.01 to 0.5% wt.

The composition may comprise a nonionic surfactant. Essentially any alkoxylated nonionic surfactants are suitable herein, for instance, ethoxylated and propoxylated nonionic surfactants. Alkoxylated surfactants can be selected from the classes of the nonionic condensates of alkyl phenols, nonionic ethoxylated alcohols, nonionic ethoxylated/propoxylated fatty alcohols, nonionic ethoxylate/propoxylate condensates with propylene glycol, and the nonionic ethoxylate condensation products with propylene oxide/ethylene diamine adducts.

The condensation products of aliphatic alcohols with from 1 to 25 moles of alkylene oxide, particularly ethylene oxide and/or propylene oxide, are suitable for use herein. The alkyl chain of the aliphatic alcohol can either be straight or branched, primary or secondary, and generally contains from 6 to 22 carbon atoms. Also suitable are the condensation products of alcohols having an alkyl group containing from 8 to 20 carbon atoms with from 2 to 10 moles of ethylene oxide per mole of alcohol.

Polyhydroxy fatty acid amides suitable for use herein are those having the structural formula $R^2CONR^1Z$ wherein: $R^1$ is H, C1-C4 hydrocarbyl, 2-hydroxyethyl 2-hydroxypropyl, ethoxy, propoxy, or a mixture thereof, for instance, C1-C4 alkyl, or C1 or C2 alkyl; and $R^2$ is a C5-C31 hydrocarbyl, for instance, straight-chain C5-C19 alkyl or alkenyl or straight-chain C9-C17 alkyl or alkenyl, or straight-chain C11-C17 alkyl or alkenyl or mixture thereof, and Z is a polyhydroxyhydrocarbyl having a linear hydrocarbyl chain with at least 3 hydroxy is directly connected to the chain, or an alkoxylated derivative (for example, ethoxylated or propoxylated) thereof. Z may be derived from a reducing sugar in a reductive amination reaction, for example, Z is a glycityl.

Suitable fatty acid amide surfactants include those having the formula: $R^1CON(R^2)_2$ wherein $R^1$ is an alkyl group containing from 7 to 21, or from 9 to 17 carbon atoms and each $R^2$ is selected from the group consisting of hydrogen, C1-C4 alkyl, C1-C4 hydroxyalkyl, and —$(C_2H_4O)_xH$, where x is in the range of from 1 to 3.

Suitable alkylpolysaccharides for use herein are disclosed in U.S. Pat. No. 4,563,647 to Llenado, having a hydrophobic group containing from 6 to 30 carbon atoms and a polysaccharide, e.g., a polyglycoside, hydrophilic group containing from 1.3 to 10 saccharide units. Alkylpolyglycosides may have the formula: $R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof In which the alkyl groups contain from 10 to 18 carbon atoms; n is 2 or 3; t is from 0 to 10, and x is from 1.3 to 8. The glycosyl may be derived from glucose.

Other suitable nonionic surfactants are food safe nonionic surfactants. Examples of food safe nonionic surfactants are sucrose esters, such as sucrose cocoate available from Croda, and sorbitan esters, such as polyoxyethylene(20) sorbitan monooleate from J.T. Baker and polyoxyethylene(20) sorbitan monolaurate from Uniquema. Other examples of food safe nonionic surfactants are given in Generally Recognised As Safe (GRAS) lists, as described below.

In a preferred embodiment, the compositions may specifically contain alkyl polyglucoside ("APG") surfactant. Suitable alkyl polyglucoside surfactants are the alkylpolysaccharides that are disclosed in U.S. Pat. No. 5,776,872 to Giret et al.; U.S. Pat. No. 5,883,059 to Furman et al.; U.S. Pat. No. 5,883,062 to Addison et al.; and U.S. Pat. No. 5,906,973 to Ouzounis et al., which are all incorporated by reference. Suitable alkyl polyglucosides for use herein are also disclosed in U.S. Pat. No. 4,565,647 to Llenado describing alkylpolyglucosides having a hydrophobic group containing from about 6 to about 30 carbon atoms, or from about 10 to about 16 carbon atoms and polysaccharide, e.g., a polyglycoside, hydrophilic group containing from about 1.3 to about 10, or from about 1.3 to about 3, or from about 1.3 to about 2.7 saccharide units. Optionally, there can be a polyalkyleneoxide chain joining the hydrophobic moiety and the polysaccharide moiety. A suitable alkyleneoxide is ethylene oxide. Typical hydrophobic groups include alkyl groups, either saturated or unsaturated, branched or unbranched containing from about 8 to about 18, or from about 10 to about 16, carbon atoms. Suitably, the alkyl group can contain up to about 3 hydroxy groups and/or the polyalkyleneoxide chain can contain up to about 10, or less than about 5, alkyleneoxide moieties. Suitable alkyl polysaccharides are octyl, nonyldecyl, undecyldodecyl tridecyl, tetradecyl, pentadecyl, hexadecyl, heptadecyl and octadecyl, di-, tri-, tetra-, penta-, and hexa-glucosides, galactosides, lactosides, glucoses, fructosides, fructoses and/or galactoses. Suitable mixtures include coconut alkyl di-, tri-, tetra-, and pentaglucosides and tallow alkyl tetra-, penta-, and hexaglucosides.

Suitable alkylpolyglycosides (or alkylpolyglucoslides) have the formula: $R^2 O(C_nH_{2n}O)_t(glucosyl)_x$ wherein $R^2$ is selected from the group consisting of alkyl, alkylphenyl, hydroxyalkyl, hydroxyalkylphenyl and mixtures thereof in which the alkyl groups contain from about 10 to about 18, preferably from about 12 to about 14, carbon atoms; n is about 2 or about 3, preferably about 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glycoside (attachment at the 1-position). The additional glycosyl units can then be attached between their 1-position and the preceding glycosyl units 2-, 3-, 4-and/or 6-position, preferably predominantely the 2-position.

A group of alkyl glycoside surfactants suitable for use in the practice of this invention may be represented by formula I below:

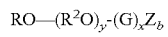
$$RO-(R^2O)_y-(G)_xZ_b \quad \text{I}$$

wherein R is a monovalent organic radical containing from about 6 to about 30 (preferably from about 8 to about 18) carbon atoms; $R^2$ is a divalent hydrocarbon radical combining from about 2 to about 4 carbon atoms; O is an oxygen atom; y is a number which has an average value from about 0 to about 1 and is preferably 0; G is a moiety derived from a reducing saccharide containing 5 or 6 carbon atoms; and x is a number having an average value from about 1 to 5 (preferably from 1.1 to 2); Z is $O_2M^1$, $O_2CR^3$, $O(CH_2)$, $CO_2M^1$, $OSO_3M^1$, or $O(CH_2)SO_3M^1$; $R^3$ is $(CH_2)CO_2M^1$ or $CH=CHCO_2M^1$; (with the proviso that Z can be $O_2M^1$ only if Z is in place of a primary hydroxyl group in which the primary hydroxyl-bearing carbon atom, $—CH_2OH$, is oxidised to form a $—CO_2M^1$ group); b is a number from 0 to 3x+1 preferably an average of from 0.5 to 2 per glycosal group; p is 1 to 10, $M^1$ is $H^+$ or an organic or inorganic cation, such as, for example, an alkali metal, ammonium, monoethanolamine, or calcium. As defined in Formula I, R is generally the residue of a fatty alcohol having from about 8 to 30 or 8 to 18 carbon atoms. Suitable alkylglycosides include, for example, APG 325® (a $C_9$-$C_{11}$ alkyl polyglycoside available from Cognis Corporation), APG 625® (a $C_{10}$-$C_{16}$ alkyl polyglycoside available from Cognis Corporation), Dow Triton® CG110 (a $C_8$-$C_{10}$ alkyl polyglyco-side available from Dow Chemical Company), AG6202® (a $C_8$ alkyl polyglycoside available from Akzo Nobel) Glucopon® 425N (a $C_8$-$C_{16}$ alkyl polyglycoside available from Cognis Corporation), Glucopon® 215 (a $C_8$-$C_{10}$ alkyl polyglycoside available from Cognis Corporation), Glucpon® 225 (a $C_8$-$C_{10}$ alkyl polyglycoside available from Cognis Corporation) and Alkadet 15® (a $C_8$-$C_{10}$ alkyl polyglycoside available from Huntsman Corporation). A C8 to C10 alkylpoly-glucoside includes alkylpoly-glucosides wherein the alkyl group is substantially C8 alkyl, substantially C10 alkyl, or a mixture of substantially C8 and C10 alkyl. Additionally, short chain APGs such as C4 and/or C6 or mixtures thereof will be suitable with the present invention.

Hydrotrope

The composition may include one or more hydrotropes for solubilizing the other components of the composition upon addition of water. The hydrotrope solubilizing materials, when used, include, but are not limited to, water soluble salts of low molecular weight organic acids such as the alkali metal (sodium and/or potassium) salts of aromatic sulfonic acids, aliphatic sulfates, aliphatic sulfonates, and aliphatic carboxylates. Specific exemplary materials include, but are not limited to, toluene sulfonate, cumene sulfonate, xylene sulfonate, naphthalene sulfonate, methyl naphthalene sulfonate, octyl sulfate, octyl sulfonate, octanoic acid, decanoic acid, and combinations thereof.

Wetting Agent

Wetting of surfaces and penetration into pores and crevices can improve cleaning and disinfection. Examples of wetting agents include ingredients described in the sections for water soluble polymers, surfactants, and hydrotropes. Other example wetting agents include, but are not limited to, nonionic water soluble polymers. These include polymers of ethylene oxide, propylene oxide, copolymers, and mixtures thereof.

Dispersant

A dispersant may be included to help remove soils and microorganism from articles and surfaces. Examples of dispersants include, but are not limited to, ingredients described in the sections for water soluble polymers, surfactants, hydrotropes, and wetting agents.

Penetrant

A penetrant increases foe rate hypochlorite ion or hypochlorous acid interacts with a soil, stain or microorganism. For example, cationic surfactants may act as phase transfer agents for the hypochlorous acid or hypochlorite ion. Particular exemplary cationic surfactants are alkyltrimethylammonium, alkylpryidinium, and alkylethylmorpholinium salts, in which the alkyl group preferably contains 4 to 18 carbon atoms, most preferably 12 to 16 carbon atoms. The alkyl chains may be linear or branched or contain an aryl group. The counterion is preferably, but not limited to, chloride, sulfate, methylsulfate, ethylsulfate, or toluene sulfonate. Other suitable cationic surfactants include dialkyldimethyl ammonium salts, in which the alkyl groups each contain 4 to 12 carbon atoms such as dioctyldimethylammonium chloride. Other suitable cationic surfactants may have two quaternary ammonium groups connected by a short alkyl chain such as N-alkylpentamethyl propane diammonium chloride. In the above cationic surfactants the methyl substituents can be completely or partially replaced by other alkyl or aryl substituents such as ethyl, propyl, butyl, benzyl, and ethylbenzyl groups, for example octyldimethylbenzyl ammonium chloride and tetrabutylammonium chloride. Cationic polymers may also function as phase transfer agents. Examples, include but are not limited, to polymers and copolymers of alkenes with quaternary ammonium groups such as vinyl alkyl trimethylammonium, vinyl N-alkyl pyridinium, and vinyl N-alkylmorpholinium. A preferred cationic polymer is DADMAC, poly diallyl dimethyl ammonium chloride.

Chelating Agent

Exemplary chelating agents include, but are not limited to, complexing agents such as the amine oxides of amino methylphosphonic acids (e.g. aminotri(methylene phosphonic acid) N-oxide and ethylenediamine tetra(methylene phosphorus acid) N,N'-dioxide), organophosphonates (e.g. 1-hydroxyethylidene-1,1-diphosphonlc acid, phosphonohydroxyacetic acid, and 2-phosphonobutane-1,2,4-tricarboxylic acid), organocarboxylates (e.g. dipicolinic acid, 2-oxa-1,3,4 butane tricarboxylate and 2-oxa-1,1,3 propane tricarboxylate), and organosulfonates (e.g. sodium xylene sulfonate and sodium methylnaphthalene sulfonate). Various anionic or zwitterionic surfactants that may bind to cations and inhibit their precipitation are also suitable chelating agents. Preferred surfactants interact with calcium ions and may be classified as lime-scale dispersants. These include C6-C18 alkyl betaines (e.g. decylbetaine and cetylbetaine), C6-C18 acyl sarcosinates (e.g. sodium lauroylsarcosinate), C6-C18 acyl C1-C6 alkyl taurates (e.g. sodium cocoylmethyltaurate), and C6-C18 alkyliminodipropionates (e.g. sodium lauryliminodipropionate), C6-C18 alkyl, aryl, or alkylaryl ether sulfates, C6-C18 alkyl, aryl, or alkylaryl ether methylsulfonates, C6-C18 alkyl, aryl, or alkylaryl ether carboxylates, sulfonated alkyldiphenyloxides (e.g. sodium dodecyldiphenyloxide disulfonate), and mono or di esters of phosphoric acid with C4-C18 alkyl, aryl, alkylaryl, alkylether, arylether and alkylarylether alcohols (e.g. disodium octyl phosphate). Various polymers and oligomers are also suitable chelating agents. These include; polycarboxylate polymers made from acrylic acid and maleic acid, optionally with copolymers of various olefins, methacrylate, styrene, methylvinylether, vinylpyrrolidone, alkenes with quaternary ammonium groups such as vinyl alkyl trimethylammonium, vinyl N-alkyl pyridinium, and vinyl N-alkylmorpholinium, etc. Sulfonate groups can be included using sulfonated styrene or other sulfonated alkenes. Polysulfonated polymeric dispersants can also be made by sulfonating various alkyl or aryl polymers. Sulfonated napthalene formaldehyde copolymers ate also useful. Typically the water soluble polymer or oligomer will have 3 to 10,000 monomer units, more preferably 20 to 2,000 monomer units. Combinations of polymers with completing agents are often more effective than either agent alone. Thus, mixtures of chelating agents from two or more of the above classes may be desired.

Odor Absorbent

While many odors are effectively controlled by hypochlorite ion or hypochlorous acid, additional ingredients to control odors may be included. Examples of odor absorbents include, but are not limited to, starches, cyclodextrins, activated carbon, zinc ricinoleate, puffed borax, silica, silica gel, fumed silica, precipitated silica, alumina, clay, and zeolites.

Fragrance

Fragrances can be included to improve the odor of the composition, the solution made by dissolving the composition in water, or the article, surface or area that is contacted by this solution. Fragrances may be a single compound such as linalool or a mixture of compounds.

Flavoring Agent

Exemplary flavoring agent may include, but are not limited to, wintergreen oil (methyl salicylate), oil of peppermint, oil of sassafras (synthetic), oil of anise, or combinations thereof.

Sweetener

In addition to a flavoring agent, the composition can include a sweetener. Suitable sweeteners include, but are not limited to, various natural and/or synthetic sweeteners (e.g., sugar alcohols) such as saccharin, stevia, aspartame, sucralose, neotame, acesulfame potassium, dextrose, sucrose, levulose (i.e., fructose), xylite, maltodextrin, sorbitol and mixtures thereof.

Colorant

Colorants may be used to color one or more parts of the solid composition, or they may be used to color the solution after the composition is dissolved in water. For example any food coloring—red, green, blue, etc. may be included. Other examples of colorants include, but are not limited to, inorganic pigments such as cobalt blue, ultramarine blue, permanganate and chromate. Organic dyes and pigments such as substituted phthalocyanines, substituted anthraquinones, substituted stilbenes, and substituted indanthrones may be suitable. Some specific examples of suitable colorants include, but are not limited to, Pigment Blue 14, Pigment Blue 15, Pigment Blue 16, Pigment Blue 28, Pigment Green 7, Pigment Green 36, Pigment Yellow 108, Direct Yellow 6, Direct Yellow 28, Direct Yellow 29, Direct Yellow 39, Direct Yellow 96.

Corrosion Inhibitors

The composition may contain precipitated or fumed colloidal silica or a silicate salt with the molar ratio of $SiO_2$ to $Na_2O$ of 1-3 to prevent dulling of metal appliances such as braces. Other examples of suitable corrosion inhibitors include, but are not limited to, zinc oxide, zinc phosphate, other phosphate salts, ascorbic acid, cinnamaldehyde, nitrites, dimethylethanolamine, phenylenediamine, hexamine, benzotriazole, benzalkonium chloride, derivatives of tannic acid, morpholine, imidazoline, aliphatic amines, borax, salts of fatty acids, salts of aliphatic or aromatic sulfonic acids, and mixtures thereof.

Viscosity Modifier

Viscosity modifiers can be included to modify the rheology of the solution after the composition is dissolved in water. Suitable thickening agents include, for example, natural and synthetic gums or gum like materials such as gum tragacanth, carboxymethylcellulose, polyvinyl pyrrolidone, and/or starch. Linear or branched polycarboxylate polymers are also suitable, especially various high molecular weight poiycarboxylates with multiple chains that are linked together as substituents on a multi-functional molecule to create a star-like molecule. Inorganic thickeners including alumina, various clays, organo-modified clays, aluminates and silicates are also suitable thickening agents. Thickening can also be achieved using combinations of oppositely charged or psuedo-charged surfactants or combinations of surfactants and polymers. Examples include combinations of anionic surfactants such as fatty acids, alkyl sulfates, or alkyl sulfonates with cationic polymers such as DADMAC, polyallyldimethylammonium chloride, combinations of cationic or psuedo cationic surfactants such as alkyl pyridinium salts, alkyltrimethyl ammonium salts alkyldimethylamine oxides, alkyl betaines, or acylsarcosinates with anionic polymers, anionic surfactants, arylsulfonates, or substituted aryl sulfonates, and surfactants such as alkylether sulfates that thicken by balancing the alkyl chain length with the number of ether linkages.

Foam Booster

Foam can be created by effervescence from the reaction of a carbonate builder with the acid. It will be enhanced by the inclusion of a surfactant. Certain combinations of surfactants will synergistically increase the amount and longevity of the foam. In addition other ingredients such as water soluble polymers and viscosity modifiers can increase the amount or longevity of the foam. The formulation can also include a foam booster to increase the amount or longevity of foam. Example foam boosters include, but are not limited to, fatty acid amides, alkoxylated fatty acid amides, fatty acid amides of alkanolamines, fatty acid amides of alkoxylated alkanolamines, and fatty acid amides of alkanolamide esters.

Defoamer

Examples of defoamers or foam control agents include, but are not limited to, alkoxylated alcohols capped with aliphatic ethers, polyglycol ethers, polyglycol esters, polyoxyethylene-polyoxypropylene block copolymers, silica, fumed silica, silicones, aminosilicones, silicone blends, and/or silicone/hydrocarbon blends and mixtures thereof.

Other Functional Ingredients

A variety of other functional ingredients can also be included depending on the intended use of the composition. Examples of other functional ingredients include, but are not limited to, stain and soil repellants, fluorescent whitening agents, enzymes, cloud point modifiers, anti-microbial agents, sporulation agents, catalysts or activators for hypochlorite ion or hypochlorous acid, and therapeutic agents.

Additional Adjuncts

The compositions optionally contain one or more of the following adjuncts: desiccants, lubricants, glidants, agglomeration aids binders, electrolytes, solubilizing agents, stabilizers, solid processing aids, preservatives, free radical inhibitors, UV protection agents, anti-oxidants, and other polymers. Binders, when used, include, but are not limited to, celluloses, starches, gums, and synthetic polymers. Solid processing aids, when used, include, but are not limited to, flow aids, lubricants, anti-static agents, and glidants. Electrolytes, when used, include, calcium, sodium and potassium chloride.

Preservatives, when used, include, but are not limited to, mildewstat or bacteriostat, methyl, ethyl and propyl parabens, phosphates such as trisodium phosphate, short chain organic acids (e.g. acetic, lactic and/or glyceric acids), bisguanidine compounds (e.g. Dantagard and/or Glydant) and/or short chain alcohols (e.g. ethanol and/or IPA). The mildewstat or bacteriostat includes, but is not limited to, mildewstats (including non-isothiazolone compounds) including Kathon GC, a 5-chloro-2-methyl-4-isothiazolin-3-one, KATHON ICP, a 2-methyl-4-isothiazolin-3-one, and a blend thereof, and KATHON 886, a 5-chloro-2-methyl-4-isothiazolin-3-one, all available from Rohm and Haas Company; BRONOPOL, a 2-bromo-2-nitropropane 1, 3 diol, from Boots Company Ltd., PROXEL CRL, a propyl-p-hydroxybenzoate, from ICI PLC; NIPASOL M, an o-phenyl-phenol, $Na^+$ salt, from Nipa Laboratories Ltd., DOWICIDE A, a 1,2-Benzoisothiazolin-3-one, from Dow Chemical Co., Nipacides from Clariant, and IRGASAN DP 200, a 2,4,4'-trichloro-2-hydroxydiphenylether, from Ciba-Geigy A.G.

Third Part

The compositions of the present invention optionally may include a third part, in one embodiment, the third part is situated between the first and second part of the solid-layered composition. The third part may include, but not limited to, the following compounds, binder, filler, colorant, desiccant, solid processing aids, a carbonate, a bicarbonate, a sesquicarbonate, a chloride, a sulfate, a phosphate, a silicate, borate, a nitrate, an aluminate, a silica-aluminate, a hydroxide, or an oxide compound of alkali metals, alkaline earths, aluminum, zinc and tin including hydrates, mono, di and tribasic compounds, mixed salts, a borate, a clay, a zeolite, and mixtures thereof. Specific examples include, but are not limited to, sodium carbonate, potassium carbonate, zinc carbonate, calcium carbonate, magnesium carbonate, sodium bicarbonate, potassium bicarbonate, magnesium bicarbonate, sodium sesquicarbonate, potassium sesquicarbonate, sodium chloride, sodium sulfate, zinc sulfate, magnesium sulfate, calcium sulfate, sodium phosphate, sodium aluminum phosphate, disodium hydrogen phosphate, sodium dihydrogen phosphate, nesosilicates, sorosilicates, cyclosilicates, inosilicates (single or double chain), phyllosilicates, tectosilicates, sodium silicate, borax, boric acid, diborates, triborates, tetraborates, metaborates, sodium nitrate, potassium nitrate, calcium nitrate, magnesium nitrate, sodium aluminate, potassium aluminate, tricalcium aluminate, alumina oxide, magnesium oxide, aluminum hydroxide, calcium hydroxide, magnesium hydroxide, calcium hydroxide, calcium oxide, zinc oxide, tin dioxide, titanium dioxide, silica alumina, and zeolite A, and mixtures thereof.

Form and Uses

The compositions of the present invention may be used in the following non-limiting examples. The composition may be used to reduce microbial or viral populations, to clean, to function as, or to treat hard surfaces, soft surfaces (i.e. fabric), toilet bowls, laundry detergent, dishwashing detergent, dentures, food wares, food surfaces, produce, meat, egg, poultry, process waters, animal quarters, and animal carcasses, water, wastes, wastewater, soil, plants, textiles, medical devices and appliances. They can be also used for therapeutic treatment of human and animal skin, nails, teeth, gums, burns, wounds, and ear, nasal and oral cavities. They may also be used to inhibit the growth of mold and to remove odors. The composition may also be used to reduce microbial or viral populations on vegetation, agricultural crops, prepared food, water used in the production or transport of foods, beverages, and bottled water. The composition of the present invention may be in the form of a powder, tablet or a granule. The present invention is directed to composition claims and methods of cleaning using the composition. The present invention may be used directly or indirectly on surfaces. Generally, methods of using the composition include: a) providing a specific surface b) contacting the surface with the claimed composition and c) optionally cleaning the surface with the composition. Another method includes: a) providing a specific surface b) adding claimed composition to a body of water or adding a body of water to claimed composition c) contacting the surface with the body of water that has contacted the composition and c) optionally, cleaning the surface with the body of water containing the composition. Another method includes: contacting an object to be cleaned with the composition in water.

Benefits

Because the composition includes calcium and/or magnesium hypochlorite and an acid, hypochlorite ion, hypochlorous acid, or a mixture thereof may formed upon dissolution of the composition in water depending on the relative amounts of these ingredients used in the composition. As such, the benefits and the performance of the composition can be tailored for the intended use. For example, the composition can be designed to convert most of the hypochlorite to hypochlorous acid in situ, when the composition is dissolved in water. Compositions that form hypochlorous acid when dissolved in water may be particularly suitable for personal care, veterinary and medical uses such as treating wounds, burns and skin. Such compositions are also useful for disinfecting medical devices including dentures and other dental appliances, as well as in other oral care environments, such as a mouthwash and as an endodontic root canal disinfectant. They may also be preferable for treating water, food, food contact surfaces and warewashing.

The use of hypochlorous acid results in a composition that is typically acidic rather than basic. This lowers pH speeds the rate of antimicrobial activity, improves the removal of plaque and biofilms including their conditioning layer, and may increases the removal of some stains. Complete removal of biofilms including their conditioning layer increases the incubation time required for bacteria to reattach to the denture to reform a biofilm when subsequently re-exposed to bacteria. Furthermore, the lower pH also increases the removal of deposits formed from hard water and the interaction of hard water with other substances such as soaps. The lower pH also increases the removal of dental calculus and other hard to remove calcium deposits. This is because the solubility of the calcium is significantly greater within the acidic environment.

When hypochlorous acid is more effective than hypochlorite ion, a lower concentration of hypochlorous acid may be used. This largely eliminates the formation of unpleasant odors from the reaction of hypochlorite ion and proteins. In addition, the hypochlorous acid works more quickly so that shorter contact times with the cleaning solution produce the desired results. Hypochlorous acid solutions by virtue of their lower effective concentration and their lower pH are also less corrosive to some materials used to construct dentures and dental appliances.

When the formation of hypochlorous acid is desired the pH of the mixed and prepared composition may be as high as about 9, preferably, the pH of the hypochlorous acid disinfecting composition is between about 5 and about 8. In another embodiment, the pH of the hypochlorous acid disinfecting composition is between about 6 and about 7. In one embodiment, the pH is preferably acidic (i.e., less than 7), most preferably between about 5.5 and about 6.5.

The nature of the application or use will also influence the selection of the concentration of hypochlorous acid or hypochlorite ion. A lower concentration is generally needed to kill microorganisms suspended in water than microorganisms dried on a surface. For example, a composition for treating water for drinking would release about 0.1 to about 20 ppm, preferably 0.5 to 15 ppm, more preferably 1 to 10 ppm of hypochlorite ion. A composition for treating waste water could release about 1 to about 200 ppm, preferably 2 to 100 ppm, more preferably 5 to 50 ppm, most preferably 10 to 25 ppm of hypochlorous acid or hypochlorite ion. In another example, a composition for treating food or food contact surfaces preferably releases about 1 to about 200 ppm of hypochlorous acid or hypochlorite ion. In another embodiment a unit dose composition for laundry releases about 5 to about 1000 ppm, preferably 10 to 600 ppm, and more preferably 50 to 400 ppm of hypochlorous acid or hypochlorite ion to the laundry washwater. For warewashing a preferred composition might release about 50 to about 200 ppm of hypochlorous acid or hypochlorite ion into either the wash water or the rinse water.

In another embodiment the compositions may be dissolved in water to form a cleaning solution that is dispensed through a spray device such as a trigger sprayer. In one example, this composition would be a cleaning product refill. The composition could be added to an empty bottle, the bottle filled with water, and the bottle closed with the dispenser or a suitable closure. After the composition dissolves, the solution could be dispensed in the usual manner. In this case the concentration of hypochlorite ion or hypochlorous acid in the solution would be about 0.1 to about 4 percent by weight, preferably 0.25 to 2.5%. It could be used for stain removal, cleaning and disinfection of hard and soft surfaces. In one embodiment it would be used to kill and remove mold in bathrooms and other area. It is also contemplated that the tablets could be dissolved in a bottle with water to make a concentrated solution containing about 1 to about 10%, preferably 2 to 8%, more preferably 4 to 6% of hypochlorite ion. Doses from this bottle could be further diluted into a bucket, wash tub or a cleaning appliance at the time of use for stain removal, cleaning or disinfection. Doses could also be applied to wash or bath water for treating skin, burns, and wounds.

EXAMPLES

The compositions described below are sample solid-layered compositions that comprise at least two parts. The compositions are useful in cleaning, sanitizing or disinfecting soft or hard surfaces.

Example 1 illustrates a sample three-part solid-layered composition of the invention.

Example 1

| First part | % wt. of first part |
| --- | --- |
| Calcium hypochlorite | 12.1% |
| Sodium carbonate | 34.5% |
| Succinic acid | 32.8% |
| Magnesium sulfate | 17.2% |
| Sodium polyacrylate (MW-5,400 daltons) | 3.4% |

| Second part | % wt. of second part |
| --- | --- |
| Sodium carbonate | 46.9% |
| Succinic acid | 44.6 |
| Sodium polyacrylate (MW-5,100 daltons) | 8.1% |
| Sodium linear alkylbenzene sulfonate | 0.4% |

| Third part | % wt. of third part |
| --- | --- |
| Sodium chloride | 100% |

Example 2 illustrates a sample three-part solid-layered composition of the invention.

Example 2

| First part | % wt. of first part |
| --- | --- |
| Calcium hypochlorite | 42.3% |
| Sodium carbonate | 29.0% |
| Succinic acid | 27.6% |
| Sodium polyacrylate (MW-5,400 daltons) | 1.1% |

| Second part | % wt. of second part |
| --- | --- |
| Sodium carbonate | 60.3% |
| Succinic acid | 34.5% |
| PVP, crosslinked | 5.2% |

| Third part | % wt. of third part |
| --- | --- |
| Sodium carbonate | 100% |

Example 3 illustrates a sample three-part solid-layered composition of the invention.

Example 3

| First part | % wt. of first part |
| --- | --- |
| Calcium hypochlorite | 15.3% |
| Sodium carbonate | 53.4% |
| Succinic acid | 30.5% |
| PVP, crosslinked | 0.8% |

| Second part | % wt. of second part |
| --- | --- |
| Succinic acid | 35.9% |
| Sodium bicarbonate | 53.9% |
| Sodium polyacrylate (MW-4,500 daltons) | 9.3% |
| Sodium linear alkylbenzene sulfonate | 0.9% |

| Third part | % wt. of third part |
| --- | --- |
| Magnesium oxide | 100% |

Example 4 Illustrates a sample three-part solid-layered composition of the invention.

Example 4

| First part | % wt. of first part |
| --- | --- |
| Calcium hypochlorite | 8.2% |
| Sodium carbonate | 45.9% |
| 3-Pyridine sulfonic acid | 37.7% |
| Polycarboxylic maleic copolymer (MW—4,500 daltons) | 4.1% |
| Laponite | 4.1% |

| Second part | % wt. of second part |
| --- | --- |
| Sodium carbonate | 41.7% |
| Succinic acid | 39.7% |
| Sodium polyacrylate (MW-5,100 daltons) | 1.0% |
| Magnesium sulfate | 17.6% |

| Third part | % wt. of third part |
| --- | --- |
| Magnesium hydroxide | 100% |

Example 5 illustrates a sample two-part solid-layered composition of the invention.

Example 5

| First part | % wt. of first part |
| --- | --- |
| Calcium hypochlorite | 8.2% |
| Sodium carbonate | 45.9% |
| Succinic acid | 37.7% |
| Sodium polyacrylate (MW-2,800 daltons) | 4.1% |
| Sodium carboxymethylcellulose | 4.1% |

| Second part | % wt. of second part |
| --- | --- |
| Sodium bicarbonate | 51.4% |
| Succinic acid | 42.2% |
| Sodium polyacrylate | 4.6% |
| Cross-linked Sodium carboxymethylcellulose | 0.9% |
| Laponite RD | 0.9% |

Example 6 illustrates a sample three-part solid-layered composition of the invention.

Example 6

| First part | % wt. of first part |
| --- | --- |
| Calcium hypochlorite | 8.2% |
| Sodium carbonate | 45.9% |
| Succinic acid | 37.7% |
| Sodium polyacrylate maleic copolymer (MW-2,800 daltons) | 8.2% |

-continued

| Second part | % wt. of second part |
|---|---|
| Sodium polyacrylate (MW-5,100 daltons) | 6.1% |
| Sodium linear alkylbenzene sulfonate | 1.4% |
| PVP, crosslinked | 0.1% |
| Glutaric acid | 8.3% |
| Potassium bicarbonate | 84.1% |

| Third part | % wt. of third part |
|---|---|
| Magnesium sulfate | 100% |

Example 7 illustrates a sample two-part solid-layered composition of the invention.

Example 7

| First part | % wt. of first part |
|---|---|
| Calcium hypochlorite | 8.2% |
| Sodium carbonate | 45.9% |
| Succinic acid | 37.7% |
| Polycarboxylic maleic copolymer (MW-4,500 daltons) | 8.2% |

| Second part | % wt. of second part |
|---|---|
| Sodium polyacrylate (MW-5,100 daltons) | 9.7% |
| Sodium linear alkylbenzene sulfonate | 2.4% |
| PVP, crosslinked | 0.1% |
| Glutaric acid | 36.2% |
| Sodium sesquicarbonate | 51.6% |

Example 8 Illustrates a sample three-part solid-layered composition of the invention.

Example 8

| First part | % wt. of first part |
|---|---|
| Calcium hypochlorite | 8.2% |
| Sodium carbonate | 45.9% |
| 3-Pyridine sulfonic acid | 37.7% |
| Polycarboxylic Maleic Copolymer (MW-4,500 daltons) | 8.2% |

| Second part | % wt. of second part |
|---|---|
| Sodium polyacrylate (MW-4,500 daltons) | 11.1% |
| Sodium bicarbonate | 49.9% |
| Sodium linear alkylbenzene sulfonate | 1.8% |
| Glutaric acid | 37.0% |
| Fragrance | 0.2% |

| Third part | % wt. of third part |
|---|---|
| Sodium sulfate | 100% |

Example 9 illustrates a sample two-part solid-layered composition of the invention.

Example 9

| First part | % wt. of first part |
|---|---|
| Calcium hypochlorite | 8.2% |
| Sodium carbonate | 45.9% |

-continued

| | |
|---|---|
| 3-Pyridine sulfonic acid | 37.7% |
| Laponite | 4.1% |
| Sodium carboxymethylcellulose | 4.1% |

| Second part | % wt. of second part |
|---|---|
| Sodium carbonate | 40.8% |
| Succinic acid | 38.8% |
| Sodium polyacrylate (MW-5,100 daltons) | 1.0% |
| Sodium lauryl sulfate | 1.4% |
| Magnesium sulfate | 17.8% |
| Fragrance | 0.2% |

Example 10 illustrates a sample two-part solid-layered composition of the invention.

Example 10

| First part | % wt. of first part |
|---|---|
| Calcium hypochlorite | 8.2% |
| Sodium carbonate | 45.9% |
| Succinic acid | 37.7% |
| Sodium polyacrylate (MW-2,800 daltons) | 4.1% |
| Sodium xylene sulfonate | 4.1% |

| Second part | % wt. of second part |
|---|---|
| Sodium bicarbonate | 47.2% |
| Blue Dye | 0.01% |
| Succinic acid | 38.6 |
| Sodium polyacrylate (MW-2,800 daltons) | 4.2% |
| Hydroxypropyl cellulose | 0.8% |
| Laponite RD | 0.8% |
| Fragrance | 0.1% |
| Cross-linked sodium carboxymethylcellulose | 4.2% |
| Dodecyl benzene sulfonic acid | 0.58% |
| Sodium sulfate | 3.51% |

Example 11 illustrates a sample two-part solid-layered composition of the invention.

Example 11

| First part | % wt. of first part |
|---|---|
| Calcium hypochlorite | 8.2% |
| Sodium carbonate | 45.9% |
| Succinic acid | 37.7% |
| Sodium polyacrylate (MW-2,800 daltons) | 4.1% |
| Microcrystalline cellulose | 4.1% |

| Second part | % wt. of second part |
|---|---|
| Sodium bicarbonate | 54.5% |
| Succinic acid | 44.4% |
| Sodium xylene sulfonate | 1% |
| Sodium sulfate | 0.1% |

Example 12 illustrates a sample two-part solid-layered composition of the invention.

Example 12

| First part | % wt. of first part |
|---|---|
| Calcium hypochlorite | 8.2% |
| Sodium carbonate | 45.9% |
| Succinic acid | 37.7% |
| Sodium polyacrylate (MW-5,100 daltons) | 4.1% |
| Microcrystalline cellulose | 4.1% |

| Second part | % wt. of second part |
|---|---|
| Sodium bicarbonate | 51.5% |
| Succinic acid | 42.0% |
| Sodium xylene sulfonate | 1.0% |
| Sodium lauryl sulfate | 5.0% |
| Sodium sulfate | 0.5% |

Example 13 illustrates a sample two-part solid-layered composition of the invention.

Example 13

| First part | % wt. of first part |
|---|---|
| Calcium hypochlorite | 8.2% |
| Sodium carbonate | 45.9% |
| Sodium sulfate | 34.8% |
| Polyacrylic Acid (MW-2,600 daltons) | 2.9% |
| Microcrystalline cellulose | 4.1% |
| Sodium polyacrylate (MW-2,800 daltons) | 4.1% |

| Second part | % wt. of second part |
|---|---|
| Sodium bicarbonate | 53.47% |
| Succinic acid | 44.93% |
| Sodium lauryl sulfate | 0.97% |
| Styrene and acrylic acid terpolymer (MW-3,000 daltons) | 0.63% |

Example 14 illustrates a sample two-part solid-layered composition of the invention.

Example 14

| First part | % wt. of first part |
|---|---|
| Calcium hypochlorite | 8.2% |
| Sodium carbonate | 45.9% |
| Sodium sulfate | 23.6% |
| Dodecyl benzene sulfonic acid | 14.1% |
| Microcrystalline cellulose | 4.1% |
| Sodium polyacrylate (MW-2,800 daltons) | 4.1% |

| Second part | % wt. of second part |
|---|---|
| Sodium bicarbonate | 52.12% |
| Succinic acid | 44.93% |
| Linear 10-carbon hydrophobe Alkyldiphenyloxide Disulfonate | 2.33% |
| Styrene and acrylic acid terpolymer (MW-3,000 daltons) | 0.62% |

Example 15 illustrates a sample two-part solid-layered composition of the invention.

Example 15

| First part | % wt. of first part |
|---|---|
| Calcium hypochlorite | 8.2% |
| Sodium carbonate | 35.9% |
| Succinic acid | 47.7% |
| Sodium polyacrylate (MW-5,100 daltons) | 4.1% |
| Microcrystalline cellulose | 4.1% |

| Second part | % wt. of second part |
|---|---|
| Sodium bicarbonate | 52.12% |
| Succinic acid | 44.93% |
| Dowfax 2A1 Branched 12-carbon hydrophobe Alkyldiphenyloxide Disulfonate | 2.33% |
| Styrene and acrylic acid terpolymer (MW-3,000 daltons) | 0.62% |

Example 16 illustrates a sample two-part solid-layered composition of the invention.

Example 16

| First part | % wt. of first part |
|---|---|
| Calcium hypochlorite | 1.0% |
| Sodium carbonate | 35.9% |
| Succinic acid | 47.7% |
| Sodium polyacrylate (MW-5,100 daltons) | 4.1% |
| Microcrystalline cellulose | 4.1% |
| Laponite RD | 7.2% |

| Second part | % wt. of second part |
|---|---|
| Sodium bicarbonate | 47.2% |
| Blue Dye | 0.01% |
| Succinic acid | 38.6 |
| Sodium polyacrylate (MW-2,800 daltons) | 4.2% |
| Hydroxypropyl cellulose | 0.8% |
| Laponite RD | 0.8% |
| Frgrance | 0.1% |
| Cross-linked sodium carboxymethylceullose | 4.2% |
| Dodecyl benzene sulfonic acid | 0.58% |
| Sodium sulfate | 3.51% |

Example 17 illustrates a sample two-part solid-layered composition of the invention.

Example 17

| First part | % wt. of first part |
|---|---|
| Calcium hypochlorite | 39.7% |
| Sodium carbonate | 27.3% |
| Sodium bisulfate | 30.4% |
| Sodium polyacrylate (MW-5,100 daltons) | 2.7% |

| Second part | % wt. of second part |
|---|---|
| Sodium bicarbonate | 76.8% |
| Sodium polyacrylate (MW-5,100 daltons) | 7.4% |
| Sodium linear alkylbenzene sulfonate | 0.7% |
| PVP, crosslinked | 3.0% |

-continued

| | |
|---|---|
| Glutaric acid | 11.8% |
| Frgrance | 0.3% |

Example 18 illustrates a sample two-part solid-layered composition of the invention.

Example 18

| First part | % wt. of first part |
|---|---|
| Calcium hypochlorite | 12.1% |
| Sodium carbonate | 34.5% |
| Succinic acid | 32.8% |
| Sodium polyacrylate (MW-5,100 daltons) | 3.4% |
| Magnesium sulfate | 17.2% |

| Second part | % wt. of second part |
|---|---|
| Sodium bicarbonate | 46.9% |
| Succinic acid | 44.6% |
| Sodium polyacrylate (MW-5,100 daltons) | 8.1% |
| Sodium linear alkylbenzene sulfonate | 0.4% |

Example 19 illustrates a sample two-part solid-layered composition of the invention.

Example 19

| First part | % wt. of first part |
|---|---|
| Calcium hypochlorite | 15.0% |
| Sodium carbonate | 52.6% |
| Adipic acid | 31.6% |
| PVP, crosslinked | 0.8% |

| Second part | % wt. of second part |
|---|---|
| Sodium bicarbonate | 47.2% |
| Blue Dye | 0.01% |
| Succinic acid | 38.6 |
| Sodium polyacrylate (MW-2,800 daltons) | 4.2% |
| Hydroxypropyl cellulose | 0.8% |
| Laponite RD | 0.8% |
| Frgrance | 0.1% |
| Cross-linked sodium carboxymethylceullose | 4.2% |
| Dodecyl benzene sulfonic acid | 0.58% |
| Sodium sulfate | 3.51% |

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

We claim:

1. A method of using a solid-layered bleach composition having at least two parts comprising a first part and a second part, comprising:
   i) dissolving the bleach composition;
   ii) providing a specific surface;
   iii) contacting the surface with the dissolved bleach composition; and
   iv) cleaning the surface with the dissolved bleach composition;
   wherein said first part comprises,
   a) 0.001%-50% by weight of a hypochlorite selected from the group consisting of calcium hypochlorite, magnesium hypochlorite and mixtures thereof;
   b) a builder selected from the group consisting of carbonate, bicarbonate, sesquicarbonate and mixtures thereof;
   c) a water-soluble polymer, wherein said water-soluble polymer is selected from the group consisting of a polycarboxylate, sulfonated carboxylate, polysulfonate, polyvinylpyrrolidone, polyquaternary ammonium salts, copolymers and mixtures thereof;
   d) at least 30% by weight of an acid selected from the group consisting of sulfonic acid, polysulfonic acid, carboxylic acid, dicarboxylic acid, polycarboxylic acid, acid sulfate, acid phosphate, phosphonic acid, and mixtures thereof;
   e) optionally, a filler selected from group consisting of chloride, sulfate, phosphate, silicate, borate, nitrate, chlorate, aluminate, silica-aluminate, hydroxide, and oxide compounds of alkali metals, alkaline earths, aluminum, zinc and tin including hydrates, mono, di and tribasic compounds, mixed salts, borates, clays, zeolites and mixtures thereof;
   f) optionally, a water-swellable polymer selected from the group consisting of cross-linked polycarboxylate, cross-linked polysulfonate, cross-linked carboxymethyl cellulose, cellulose, sodium carboxymethylcellulose, and mixtures thereof;
   g) optionally, desiccants, solid processing aids, colorants, agglomeration aids, binders, glidants, corrosion inhibitors, and mixtures thereof; and
   h) wherein said first part does not contain sodium hypochlorite, lithium hypochlorite, potassium hypochlorite, sodium chlorite, chlorine dioxide, N-halogenated compounds, hydantoins, isocyanurates, carboxylic acids that also have hydroxyl, amino, amido, imino, or imido groups, enzymes; and
   wherein said second part comprising,
   a) a functional ingredient selected from the group consisting of a surfactant, a hydrotrope, a wetting agent, a dispersant, a penetrant, a chelating agent, an odor absorbent, a fragrance, a flavoring agent, a sweetener, a colorant, a corrosion inhibitor, a viscosity modifier, a foam booster, a defoamer, a stain and soil repellant, a fluorescent whitening agent, an enzyme, a cloud point modifier, an anti-microbial agent, a sporulation agent, a catalyst, an activating agent, a therapeutic agent, and mixtures thereof;
   b) a builder or filler selected from the group consisting of a carbonate, a bicarbonate, a sesquicarbonate, a chloride, a sulfate, a phosphate, a silicate, borate, a nitrate, an aluminate, a silica-aluminate, a hydroxide, or an oxide compound of alkali metals, alkaline earths, aluminum, zinc and tin including hydrates, mono, di and tribasic compounds, mixed salts, a borate, a clay, a zeolite, and mixtures thereof;
   c) optionally acids, water soluble polymers, disintegrants, desiccants, solid processing aids, agglomeration aids, binders, glidants, preservatives, and mixtures thereof; and
   d) wherein said second part does not contain any oxidant wherein said oxidant comprises hypochlorite, chlorite, chlorate, perchlorate, N-halo compound, chlorine dioxide, peracid, peroxide, peroxygen bleach and mixtures thereof.

2. The method of claim 1, wherein the second part contains a builder selected from carbonate, bicarbonate, sesquicarbonate and mixtures thereof and the second part contains an acid selected from the group consisting of sulfonic acid, a carboxylic acid, a dicarboxylic acid, acid sulfate, an acid phosphate, a phosphonic acid, and mixtures thereof.

3. The method of claim 1, wherein none of the ingredients are coated, encapsulated or embedded in a polymer, resin, or a wax.

4. The method of claim 1, wherein the functional ingredient in the second part contains both the surfactant and the hydrotrope.

5. The method of claim 4, wherein the hydrotrope in the second part is a salt selected from the group consisting of toluene sulfonate, cumene sulfonate, xylene sulfonate, naphthalene sulfonate, methyl naphthalene sulfonate, C4-C10 alkane sulfonates, and C6-C10 carboxylates, and mixtures thereof.

6. The method of claim 4, wherein the surfactant in the second part is an anionic surfactant.

7. The method of claim 1, wherein the acid in the first part is the dicarboxylic acid.

8. The method of claim 1, wherein the water-soluble polymer in the first part is the polycarboxylate, and the polycarboxylate is selected from the group consisting of maleic acid, acrylic acid, methacrylic acid and mixtures thereof.

9. The method of claim 8, wherein the molecular weight of the polycarboxylate is between 1,000-6,000 daltons.

10. The method of claim 1, wherein the composition requires a third part wherein said third part is situated between the first part and second part and said third part comprises a component selected from the group consisting of binder, filler, colorant, desiccant, solid processing aids, sodium chloride, sodium silicate, sodium sulfate, magnesium sulfate, magnesium carbonate, calcium carbonate, calcium hydroxide, calcium oxide, magnesium oxide, magnesium hydroxide, sodium carbonate, potassium carbonate, sodium bicarbonate, sodium sesquicarbonate, potassium sesquicarbonate, sodium borate, boric acid, aluminum hydroxide, silica and mixtures thereof.

11. The method of claim 1, wherein the composition is in the form of a tablet.

12. The method of claim 1, wherein the composition is in the form of a granule.

13. The method of claim 1, wherein the surface is a soft surface.

14. The method of claim 1, wherein the surface is a hard surface.

15. A method of using a solid-layered bleach composition having at least two parts comprising a first part and a second part, comprising:
  a) dissolving the bleach composition;
  b) providing a specific surface;
  c) contacting the surface with the dissolved bleach composition; and
  d) cleaning the surface with the dissolved bleach composition;
wherein said first part consisting essentially of,
  a) 0.001%-50% by weight of a hypochlorite selected from the group consisting of calcium hypochlorite, magnesium hypochlorite and mixtures thereof
  b) a builder selected from the group consisting of carbonate, bicarbonate, sesquicarbonate and mixtures thereof
  c) a water-soluble polymer, wherein said water-soluble polymer is selected from the group consisting of a polycarboxylate, sulfonated carboxylate, polysulfonate, polyvinylpyrrolidone, polyquaternary ammonium salts, copolymers and mixtures thereof;
  d) at least 30% by weight of an acid selected from the group consisting of sulfonic acid, polysulfonic acid, carboxylic acid, dicarboxylic acid, polycarboxylic acid, acid sulfate, acid phosphate, phosphonic acid, and mixtures thereof;
  e) optionally, a filler selected from group consisting of chloride, sulfate, phosphate, silicate, borate, nitrate, chlorate, aluminate, silica-aluminate, hydroxide, and oxide compounds of alkali metals, alkaline earths, aluminum, zinc and tin including hydrates, mono, di and tribasic compounds, mixed salts, borates, clays, zeolites and mixtures thereof;
  f) optionally, a water-swellable polymer selected from the group consisting of cross-linked polycarboxylate, cross-linked polysulfonate, cross-linked carboxymethyl cellulose, cellulose, sodium carboxymethylcellulose, and mixtures thereof;
  g) optionally, desiccants, solid processing aids, colorants, agglomeration aids, binders, glidants, corrosion inhibitors, and mixtures thereof; and
  h) wherein said first part does not contain sodium hypochlorite, lithium hypochlorite, potassium hypochlorite, sodium chlorite, chlorine dioxide, N-halogenated compounds, hydantoins, isocyanurates, carboxylic acids that also have hydroxyl, amino, amido, imino, or imido groups, enzymes; and
wherein said second part consisting essentially of,
  a) a functional ingredient selected from the group consisting of a surfactant, a hydrotrope, a wetting agent, a dispersant, a penetrant, a chelating agent, an odor absorbent, a fragrance, a flavoring agent, a sweetener, a colorant, a corrosion inhibitor, a viscosity modifier, a foam booster, a defoamer, a stain and soil repellant, a fluorescent whitening agent, an enzyme, a cloud point modifier, an anti-microbial agent, a sporulation agent, a catalyst, an activating agent, a therapeutic agent, and mixtures thereof;
  b) a builder or filler selected from the group consisting of carbonate, bicarbonate, sesquicarbonate, chloride, sulfate, phosphate, silicate, borate, nitrate, aluminate, silica-aluminate, hydroxide, or oxide compound of alkali metals, alkaline earths, aluminum, zinc and tin including hydrates, mono, di and tribasic compounds, mixed salts, borates, clays, zeolites, and mixtures thereof;
  c) optionally, a water-soluble polymer selected from the group consisting of a polycarboxylate, sulfonated carboxylate, polysulfonate, polyvinylpyrrolidone, polyquaternary ammonium salts, copolymers and mixtures thereof;
  d) optionally, an acid selected from the group consisting of sulfonic acid, polysulfonic acid, carboxylic acid, dicarboxylic acid, polycarboxylic acid, acid sulfate, acid phosphate, phosphonic acid, and mixtures thereof;
  e) optionally, a water-swellable polymer wherein said water-swellable polymer is selected from the group consisting of cross-linked polycarboxylate, cross-linked polysulfonate, cross-linked carboxymethyl cellulose, cellulose, sodium carboxymethylcellulose, and mixtures thereof; and
  f) optionally, desiccants, solid processing aids, agglomeration aids, binders, glidants, preservatives, and mixtures thereof; and
  g) wherein said second part does not contain any oxidant, wherein said oxidant comprises hypochlorite, chlorite, chlorate, perchlorate, N-halo compound, chlorine dioxide, peracid, peroxide, peroxygen bleach and mixtures thereof.

16. The method of claim 15, wherein none of the ingredients are coated, encapsulated or embedded in a polymer, resin, or a wax.

17. The method of claim 15, wherein the second part contains a builder selected from carbonate, bicarbonate, sesquicarbonate and mixtures thereof and an acid in the second part selected from the group consisting of sulfonic acid, a carboxylic acid, a dicarboxylic acid, acid sulfate, an acid phosphate, a phosphonic acid, and mixtures thereof.

18. The method of claim 15, wherein the functional part of the second part contains the surfactant and the hydrotrope.

19. The method of claim 15, wherein the water-soluble polymer is a polycarboxylate and the acid is a dicarboxylic acid.

20. The method of claim 15, wherein the composition requires a third part wherein said third part is situated between the first part and second part and said third part consists essentially of a component selected from the group consisting of binder, filler, colorant, desiccant, sodium chloride, sodium silicate, sodium sulfate, magnesium sulfate, magnesium carbonate, calcium carbonate, calcium hydroxide, calcium oxide, magnesium oxide, magnesium hydroxide, sodium carbonate, potassium carbonate, sodium bicarbonate, sodium sesquicarbonate, potassium sesquicarbonate, sodium borate, boric acid, aluminum hydroxide, silica and mixtures thereof.

* * * * *